(12) United States Patent
Gramatte et al.

(10) Patent No.: US 7,943,176 B2
(45) Date of Patent: May 17, 2011

(54) ORAL DOSAGE FORM FOR PROPIVERINE OR ITS PHARMACEUTICALLY ACCEPTABLE SALTS WITH AN EXTENDED RELEASE OF THE ACTIVE INGREDIENT

(75) Inventors: Thomas Gramatte, Dresden (DE); Peter Gruber, Merzhausen (DE); Michael Heschel, Pirna (DE); Dirk Pamperin, Dresden (DE); Jan Ploen, Dresden (DE); Steffen Scheithauser, Dresden (DE); Wolfgang Wehner, Borthen (DE); Peter Guldner, Dresden (DE)

(73) Assignee: Apogepha Arzneimittel GmbH, Dresden (DE)

( * ) Notice: Subject to any disclaimer, the term of this patent is extended or adjusted under 35 U.S.C. 154(b) by 1151 days.

(21) Appl. No.: 10/492,270

(22) PCT Filed: Oct. 8, 2002

(86) PCT No.: PCT/EP02/11253
§ 371 (c)(1),
(2), (4) Date: Apr. 8, 2004

(87) PCT Pub. No.: WO03/030869
PCT Pub. Date: Apr. 17, 2003

(65) Prior Publication Data
US 2004/0258749 A1 Dec. 23, 2004
US 2008/0317848 A2 Dec. 25, 2008

(30) Foreign Application Priority Data
Oct. 9, 2001 (DE) .................................. 101 49 674

(51) Int. Cl.
A61K 9/14 (2006.01)
(52) U.S. Cl. ........ 424/489; 424/490; 424/494; 424/451; 424/457; 424/461; 514/317
(58) Field of Classification Search .................... None
See application file for complete search history.

(56) References Cited

U.S. PATENT DOCUMENTS

| | | | | |
|---|---|---|---|---|
| 5,178,868 A | * | 1/1993 | Malmqvist-Granlund et al. | 424/490 |
| 5,912,268 A | | 6/1999 | Guittard et al. | 514/534 |
| 6,962,717 B1 | * | 11/2005 | Huber et al. | 424/490 |
| 7,138,405 B2 | * | 11/2006 | Wyllie | 514/272 |
| 2001/0005728 A1 | * | 6/2001 | Guittard et al. | 514/534 |
| 2002/0010216 A1 | * | 1/2002 | Rogosky et al. | 514/649 |
| 2003/0064036 A1 | * | 4/2003 | Petereit et al. | 424/49 |

FOREIGN PATENT DOCUMENTS

| | | |
|---|---|---|
| AU | 764469 | 8/2000 |
| DE | 29 37 489 | 4/1980 |
| DE | 100 16 356 | 10/2001 |
| DE | 100 16 356 A1 | 10/2001 |
| DE | 101 49 674 | 4/2003 |
| EP | 0032562 | 3/1984 |
| EP | 0069259 | 1/1985 |
| EP | 0 253 541 | 1/1988 |
| EP | 0 365 947 | 5/1990 |
| EP | 497977 | 10/1990 |
| EP | 0068191 | 9/1991 |
| EP | 1229026 A1 | 11/2000 |
| EP | 1 064 938 | 1/2001 |
| EP | 1123705 A1 | 2/2001 |
| EP | 1123705 * | 8/2001 |
| EP | 1 273 301 A2 | 1/2003 |
| GB | 2031727 | 11/1982 |
| JP | 63-23814 | 2/1988 |
| JP | 63-154619 | 6/1988 |
| JP | 2164821 | 6/1990 |
| JP | 9501445 | 10/1997 |
| JP | 11505264 | 5/1999 |
| JP | 2001-39873 | 2/2001 |
| JP | 2001039873 | 2/2001 |
| JP | 2001048783 | 2/2001 |
| JP | 2002-535353 | 10/2002 |
| JP | 2003-503341 | 1/2003 |
| JP | 2003-513033 | 4/2003 |
| WO | 95/23593 | 9/1995 |
| WO | WO 95/23593 | 9/1995 |
| WO | 96/12477 | 5/1996 |
| WO | 96/37202 | 11/1996 |
| WO | WO 96/37202 | 11/1996 |
| WO | WO 9709980 * | 3/1997 |
| WO | 97/12605 | 4/1997 |
| WO | 97/37640 | 10/1997 |
| WO | 98/18610 | 5/1998 |
| WO | 98/32425 | 7/1998 |

(Continued)

OTHER PUBLICATIONS

Laicher et al.—Theophyllin, "Die Pellet-Technologie", Arzneim-Forsch./Drug Res. 48(I), Nr. 5a (1998), pp. 540-547.

Grunenberg et al.—Theophyllin, "Erfahrungen bei der Ubertragung des Filmcoating-Prozessess fur Theophyllin-Retardpellets in den ProduktionsmaBstab", Arzneim-Forsch./Drug Res. 48(I), Nr. 5a (1998), pp. 547-551.

Fuchs et al.—Theophyllin, "EinfluB verschiedener Variablen auf die In-vitro-Freisetzung eines Theophyllin-Retardpraparates", Arzneim-Forsch./Drug Res. 48(I), Nr. 5a (1998), pp. 552-556.

Fuchs et al.—Theophyllin, Anforderungen an die Produktqualitat von Theophyllin-Retardpraparaten, Arzneim-Forsch./Drug Res. 48(I), Nr. 5a (1998), pp. 556-561.

Wilson et al.—Theophyllin, "Wirkung der Vorbehandlung mit Ranitidin auf Pharmakokinetik und gastrointestinale Passage eines Theophyllin Retard-Praparates", Arzneim-Forsch./Drug Res. 48(I), Nr. 5a (1998), pp. 561-568.

(Continued)

Primary Examiner — Robert A. Wax
Assistant Examiner — Hasan S Ahmed
(74) Attorney, Agent, or Firm — Vidas, Arrett & Steinkraus

(57) ABSTRACT

By suitable retardation oral pharmaceutical compositions containing propiverine or one or several pharmaceutically acceptable salts thereof in an amount of 4 mg to 60 mg propiverine and having a prolonged release of the active agent are produced. Preferably a blend of active agent and optionally one or more acidic substances having a $pK_a$ value of less than 6.65 are provided with a retarding coating or are embedded in a matrix which is then optionally coated with further retarding layers.

19 Claims, 6 Drawing Sheets

FOREIGN PATENT DOCUMENTS

| | | |
|---|---|---|
| WO | 00/12069 | 3/2000 |
| WO | 00/27369 | 5/2000 |
| WO | 00/44353 A1 | 8/2000 |
| WO | WO 00/44353 | 8/2000 |
| WO | WO 00/44353 A1 | 8/2000 |
| WO | 01/34579 A1 | 5/2001 |
| WO | WO 01/32149 | 5/2001 |
| WO | 01/62236 A2 | 8/2001 |
| WO | 02/060415 A1 | 8/2002 |
| WO | 02/067906 A1 | 9/2002 |
| WO | 03/030869 | 4/2003 |

OTHER PUBLICATIONS

Pabst et al.—Theophyllin, "Untersuchung von nahrungsbedingten Veranderungen der Theophyllin-Resorption", Arzneim-Forsch./Drug Res. 48(I), Nr. 5a (1998), pp. 569-573.

Pabst et al.—Theophyllin, "Absorptionsprofil und absolute Bioverfugbarkeit eines Theophyllin-Retardpraparats", Arzneim-Forsch./Drug Res. 48(I), Nr. 5a (1998), pp. 574-579.

von Niecieck et al.—Theophyllin, "In-vivo-Verifizierung der In-vitro-Freisetzungsspezifikation eines Theophyllin-Retardpraparats", Arzneim-Forsch./Drug Res. 48(I), Nr. 5a (1998), pp. 580-583.

Pabst et al.—Theophyllin, "Revalidierung der In-vitro-Spezifikationsgrenzen anhand einer In-vitro-/In-vivo-Korrelation", Arzneim-Forsch./Drug Res. 48(I), Nr. 5a (1998), pp. 584-588.

Fuchs et al.—Theophyllin, Pharmakokinetik einer Theophyllin-Retardformulierung nach einmal und zweimal taglicher Mehrfachdosierung, Arzneim-Forsch./Drug Res. 48(I), Nr. 5a (1998), pp. 589-592.

Witschital et al.—Theophyllin, "Pharmakokinetik von Theophyllin in einer Retardformulierung bei jugendlichen Asthmatikern", Arzneim-Forsch./Drug Res. 48(I), Nr. 5a (1998), pp. 593-596.

Fuchs et al.—Theophyllin, "Einfluß einer Gallenausschuttung auf die Pharmakokinetik eines Theophyllin-Retardpraparates", Arzneim-Forsch./Drug Res. 48(I), Nr. 5a (1998), pp. 597-604.

Taro Ogiso et al, "Comparison of the in Vitro Skin Penetration of Propiverine with That of Terodiline" Biol. Pharm. Bull. vol. 19 No. 7 (1995) pp. 968-975.

G.H.P. Te Wierik et al. "A new generation starch product as excipient in pharmaceutical tablets III. Pharameters affecting controlled drug release from tablets based on high surface area retrograded pregelatinized potato starch", International Journal of Pharmaceutics 157 (1997) pp. 181-187.

Thoma et al., Retardierung Schwach basische Arzneistoffe, "1. Mitt.: Behebung der Verfugbarkeitsprobleme von Noscapin aus Diffusionspellets", Pharm. Ind, 51 Nr. 1 (1989) pp. 98-101.

Thoma et al., Retardierung Schwach basische Arzneistoffe, "2. Mitt.: Verbesserung der Verfugbarkeit von Papaverin und Codein aus Diffusionspellets", Pharm. Ind, 51 Nr. 5 (1989) pp. 540-543.

Thoma et al., Retardierung Schwach basische Arzneistoffe, "3. Mitteilung: Verbesserung der Verfugbarkeit von Phenothiazin-Neuroleptika aus Tabletten mit Diffusionsuberzugen", Pharm. Ind, 51 Nr. 1 (1991) pp. 69-73.

Thoma et al., Retardierung Schwach basische Arzneistoffe, "4. Mittelung: Behebung der Verfugbarkeitsprobleme von Vincamin aus Diffusions-Depotarzneiformen", Pharm. Ind, 51 Nr. 6 (1991) pp. 595-600.

Thoma et al., Retardierung Schwach basische Arzneistoffe, "5. Mittelung: Verbesserung der Freisetzung von Dihydroergotaminmethansulfonat bei Diffusions-Depotarzneiformen", Pharm. Ind, 51 Nr. 7 (1991) pp. 686-690.

Thoma et al., Retardierung Schwach basische Arzneistoffe, "6. Mittelung: Verbesserung der Freisetzung und Verfugbarkeit von Dihydroergotaminmethansulfonat mit Hilfe magensaftresistenter Filmuberzuge", Pharm. Ind, 53 Nr. 8 (1991) pp. 778-785.

English Translation of Office Action for JP Application No. 2003-533902 dated Jan. 29, 2008.

Laicher et al.-Theophylline, "Pellet Technology," Arzneim-Forsch./Drug Res. 48(I), No. 5a (1998), pp. 540-547.

Grunenberg et al.-Theophylline, "Experience in Scaling-up the Film Coating Process for Theophylline Sustained Release Pellets," Arzneim-Forsch./Drug Res. 48(I), No. 5a (1998), pp. 547-551.

Fuchs et al.-Theophylline, "Influence of Different Varibles on the in vitro Dissolution of a Theophylline Sustained Release Dosage Form," Arzneim-Forsch./Drug Res. 48(I), No. 5a (1998), pp. 552-556.

Fuchs et al.-Theophylline, "Product Quality Requirements of Theophylline Sustained Release Dosage Forms," Arzneim-Forsch./Drug Res. 48(I), No. 5a (1998), pp. 556-561.

Wilson et al.-Theophylline, "Effect of Pretreatment with Ranitidine on the Pharmacokinetics and Gastrointestinal Transit of a Sustained Release Theophylline Preparation," Arzneim-Forsch./Drug Res. 48(I), No. 5a (1998), pp. 561-568.

Pabst et al.-Theophylline, "Study on the Influence of Food on the Absorption of Theophylline," Arzneim-Forsch./Drug Res. 48(I), No. 5a (1998), pp. 569-573.

Pabst et al.-Theophylline, "Absorption Profile and Absolute Bioavailability of a Theophylline Sustained Release Preparation," Arzneim-Forsch./Drug Res. 48(I), No. 5a (1998), pp. 574-579.

von Nieciecki et al.-Theophylline, "In vivo Verification of the In-vitro Release Specification of a Sustained Release Theophylline Preparation," Arzneim-Forsch./Drug Res. 48(I), No. 5a (1998), pp. 580-583.

Pabst et al.-Theophylline, "Revalidation of in Bitro Specification Limits following an In Vitro/In Vivo Correlation," Arzneim-Forsch./Drug Res. 48(I), No. 5a (1998), pp. 584-588.

Fuchs et al.-Theophylline, "Pharmacokinetics of a Sustained Release Theophylline Preparation Following Once-a-day and twice-a-day Multiple Dosing," Arzneim-Forsch./Drug Res. 48(I), No. 5a (1998), pp. 589-592.

Witschital et al.-Theophylline, "Pharmacokinetics of a Sustained Release Theophylline Preparation in Young Asthmatics," Arzneim-Forsch./Drug Res. 48(I), No. 5a (1998), pp. 593-596.

Fuchs et al.-Theophylline, "Effect of Cholagogia on the Pharmacokinetic Profile of a Sustained Release Theophylline Formulation," Arzneim-Forsch./Drug Res. 48(I), No. 5a (1998), pp. 597-604.

Thoma et al., Retardation of Weakly Basic Drugs, "First Communication: Improving Availability Problems of Noscapine in Diffusion Pellets," Pharm. Ind, 51, No. 1 (1989) pp. 686-690.

Thoma et al., Retardation of Weakly Basic Drugs, "Second Communication: Optimizing Availability of Papaverine and Codeine in Diffusion Pellets," Pharm. Ind, 51, No. 5 (1989) pp. 540-543.

Thoma et al., Retardation of Weakly Basic Drugs, "Third Communication: Improving the Availability of Phenothiazine Neuroleptics from Tablets with Diffusion Membranes," Pharm. Ind, 51, No. 1 (1991) pp. 69-73.

Thoma et al., Retardation of Weakly Basic Drugs, "Fourth Communication: Solving Availability Problems of Vincamine in Diffusion Dosage Forms," Pharm. Ind, 51, No. 6 (1991) pp. 595-600.

Thoma et al., Retardation of Weakly Basic Drugs, "Fifth Communication: Improving the Release of Dihydroergotamine Methane Sulfonate from Diffusion Dosage Forms," Pharm. Ind, 51, No. 7 (1991) pp. 686-690.

Thoma et al., Retardation of Weakly Basic Drugs, "Sixth Communication: Improving the Release and Availability of Dihydroergotamine Methane Sulfonate with the aid of Enteric Coatings," Pharm. Ind, 51, No. 8 (1991) pp. 778-785.

Iwatsubo et al. "Clinical effects of propiverine hydrochloride for uninhibited neurogenic bladder disorders." Nishinihon Journal of Urology 1990, vol. 52, No. 2, p. 233-240.

Pharmacia & Upjohn, CL 309-2000, "Metodo Terapeutico Y Formulacion," publication date unknown, together with unverified Google machine translation of OCR text of CL 309-2000. CL 309-2000 is considered likely to be a non-priority equivalent of WO 0012069 based on similarity of translated claim 1 and of the inventor names.

* cited by examiner

ORAL DOSAGE FORM FOR PROPIVERINE OR ITS PHARMACEUTICALLY ACCEPTABLE SALTS WITH AN EXTENDED RELEASE OF THE ACTIVE INGREDIENT

This application claims priority of German patent application 101 49 674, filed Oct. 9, 2001, incorporated herein by reference.

The invention relates to novel oral dosage forms of propiverine or pharmaceutically acceptable salts thereof having a prolonged release of the active agent.

Propiverine—the chemical name of it is: 2,2-diphenyl-2-(1-propoxy)acetic acid(1-methyl-piperid-4-yl)ester or one of the pharmaceutically acceptable salts thereof are generally known for the treatment of hypertonic functional states in the bladder region (over-active bladder) (see DE 2937589 incorporated herein by reference).

The bladderspasmolytic propiverine acts as an anticholinergic in that it immobilises the cholinergic/muscarineric utilised smooth musculature of the bladder by blocking of the corresponding receptors. Furthermore there is a directed influence on the calcium household of the cell in the meaning of an increase of the effect.

Propiverine in the form of its hydrochloride in rapidly releasing oral dosage forms in several preparations, e.g. Mictonorm®, has been on the market for years. The dosage used so far of e.g. three times a day of one pill of Mictonorm® at 15 mg propiverine-hydrochloride each results in relatively heavily fluctuating blood levels with repeated daily peaks. Because of the anticholinergic effect of propiverine typical anticholinergic side effects like and accommodation disorders have to be accepted with a rapid increase of the blood level. Therefore these side effects limit the amount of the possible unit dose of non-modified, rapidly releasing dosage forms to 10-20 mg.

For a therapeutically active blood level of propiverine the exact compliance up-take intervals are thus necessary, which lead to problems, in particular with elder patients who are the main group having hypertonic functional states of the bladder.

For these reasons it is desirable to reduce the repeated dose each day with all its known effects to a once a day dose having the same or improved therapeutic effect.

In order to realise suitable oral dosage forms with a sufficiently delayed release of the active agent and a therapeutically effective blood level for an interval of 24 hours one has to take into account that such formulations naturally release substantial portions of its content of active agent in the lower intestine regions.

It is generally known from a pharmacokinetical point of view that the resorption rate essentially determines the temporary building-up of a blood level and that the quantitative extent of the resorption as well as the half-life period of the substance in the organism decide whether at the end of the dosage intervals, i.e. before administration of the next dose, effective blood levels can be maintained. A sufficient resorption rate and a sufficient extent of the resorption of the active agent over the whole region of the gastrointestinal tract with its different pH values are thus necessary.

The weak basic propiverine having a $pK_a$ value of 7.35±0.1 (water, 25° C.) according to general teachings should relatively badly resort in prolonged form in the stomach, but as a base, i.e. as the weak basic neutral form, it should be relatively well resorbed in the intestinal tract.

Since, however, the inner surface of the intestine is coated with a microscopically thin layer of water the solubility and the lipophility of the base to be resorbed are of decisive importance beside the acid base properties of a substance.

The distribution coefficient and the solubility of propiverine-hydrochloride in dependence of the pH value are known (determination of the amount of propiverine in the aqueous phase via HPLC).

Distribution coefficient of propiverine-hydrochloride (1-octanol/water, 25° C.)

| pH | K [mean values, measured three times] | Log [K] |
| --- | --- | --- |
| 1.0 | 22 | 1.3 |
| 5.0 | 13 | 1.1 |
| 6.0 | 227 | 2.4 |
| 6.5 | 884 | 2.9 |
| 6.8 | 6904 | 3.8 |
| 7.0 | 10346 | 4.0 |
| 7.2 | 15438 | 4.2 |
| 7.5 | 26068 | 4.4 |
| 8.0 | 52372 | 4.7 |

Solubility of propiverine-hydrochloride in water

| pH | Temperature [° C.] | Solubility [g/l] |
| --- | --- | --- |
| 5.8 | 24 | >200 |
| 5.8 | 37 | 368 |
| 6.0 | 24 | 209 |
| 7.0 | 24 | 1.2 |
| 7.2 | 24 | 1.1 |

These physiochemical properties of propiverine-hydrochloride are thus not suitable for the realisation of a delayed (retarded) formulation since in the aqueous phase a sufficient solubility is only given in the acidic region which is the unfavourable resorption region for propiverine because of its protonation. In the more favourable pH range for resorption above a pH of 6.65 there is, however, practically insolubility, and the lipophilic propiverine base precipitates. Furthermore it is known from practical experiences that with the beginning precipitation of the base even smallest amounts of propiverine-hydrochloride are coated with insoluble propiverine base, and any further transition into the corresponding base ceases. This substance properties of the propiverine-hydrochloride appear to render the realisation of a 12 or 24 hour depot not very promising. Because of these reasons mentioned, experiments for the realisation of transdermal systems have failed (Biol. Pharm. Bull. 1995, 18(7), 968-975).

Furthermore it is known that propiverine shows an extraordinarily strong first pass effect by monooxygenase to the undesirable propiverine-N-oxide which puts a strain on the organism. Propiverine-N-oxide with its quaternary, permanently positive charged nitrogen is very well soluble in water (solubility of >127 to >99 g/l at pH=4.0-8.0) in the whole pH range in contrast to propiverine, and is thus worse to resorb.

The monooxygenases present in the intestine oxidise the propiverine base present in equilibrium to the N-oxide. Therewith the excretion of propiverine is possible via its water-soluble N-oxide. This pharmacokinetic substance property of propiverine appears to make the realisation of a 24 hours depot releasing in the lower intestine sections with a therapeutically effective level or bioequivalence, respectively, not very promising with the rapid release dosage from currently on the market.

Apart from propiverine the tertiary amine oxybutynine and tolterodine are common standard in therapy for the treatment of hypertonic function states of the bladder. The half-time period as the main pharmacokinetic criterion is only 2-3 hours for the rapidly releasing dosage forms of oxybutynine and tolterodine currently on the market, the half-time period for propiverine, however, is 15 hours.

By means of several galenic techniques oral dosage forms having a delayed release of the active agent have been realised for oxybutynine (U.S. Pat. No. 5,912,268, WO 9523593, WO 9612477, WO 0737202) and tolterodine (WO 0012069, WO 0027369).

In the case of propiverine such a dosage form appears to make little sense or the long half-life period may even be in conflict with a successful realisation of a therapeutically usable formulation.

For weak basic drugs oral dosage forms having a delayed release of the active agent generally form prior art as single-unit formulation and also as multiple-unit formulation.

In controlled releasing single-unit forms, for example matrix tablets, multiple-layer tablets, diffusion tablets, an additional diffusion control, for example by means of tartaric acid (Int. J. Pharm. 1997, 157, 181-187) or by means of succinic acid (Pharm. Ind. 1991, 53, 686-690) is achieved. When chewing such a monolithic form a high amount of active agent would be suddenly released despite of retardation, which would be problematic in the case of highly active anticholinergic agents with respect to medicament security.

Multiple-unit dosage forms do not show these disadvantages and are also described for weakly basic drugs (Pharm. Ind. 1989, 51, 98-101, 540-543; Pharm. Ind. 1991, 53, 69-73, 596-600, 778-785; Arzneim.-Forsch./Drug Res. 1998, 48, 540-604). Further technical solutions of pH-dependent and in the basic region badly soluble compounds exist for example for dipyridamol (EP 32562; EP 68191) and for bromohexine (EP 69259).

It is the object of the invention despite of physicochemical and pharmacokinetic properties of propiverine and its salts which seem to be disadvantages, to produce oral dosage forms of said active agent having a prolonged release for the first time, which independently of the pH value of the whole gastrointestinal tract, independently of potential disorders of the gastro and intestinal peristaltics as well as relatively independently of inter- and intraindividual differences of patients show over a period of 24 hours a constant blood level which is clinically relevant for the treatment of an over-active bladder which simultaneously decreased rate of side effects.

The solution of the object according to the invention follows from the features of the independent claim. Advantageous embodiments are defined in the dependent sub-claims.

According to a preferred embodiment, the object is preferably solved in that oral dosage forms are realised which contain propiverine and/or one pharmaceutically acceptable salt thereof in a therapeutically effective amount, corresponding to 4 mg to 60 mg propiverine, and which show the following in vitro release rates—measured in 750 ml 0.1 NCl during the first hour and subsequently measured in 750 ml USP-buffer at pH=5.8 using the Ph. Euro. basket method at 100 rpm and 37° C.:

| 0-20% | propiverine, released after | 1 hour |
| 10-45% | propiverine, released after | 3 hours |
| 30-60% | propiverine, released after | 5 hours |
| 40-75% | propiverine, released after | 7 hours |

-continued

| 50-80% | propiverine, released after | 9 hours |
| >60% | propiverine, released after | 12 hours, and particularly preferred |
| 60-90% | propiverine, released after | 12 hours, | which show a clinically relevant blood level over a prolonged period of time, bioequivalence to the rapidly releasing preparation currently on the market, a reduced rate of side effects and finally an improved patient-compliance because of the possibility of a once a day administration.

For the first time disadvantages resulting from the physicochemical and pharmacokinetic properties of the drug propiverine and prejudices resulting from the long half-life period have been overcome and simultaneously a therapeutic progress has been achieved.

Figure 1:
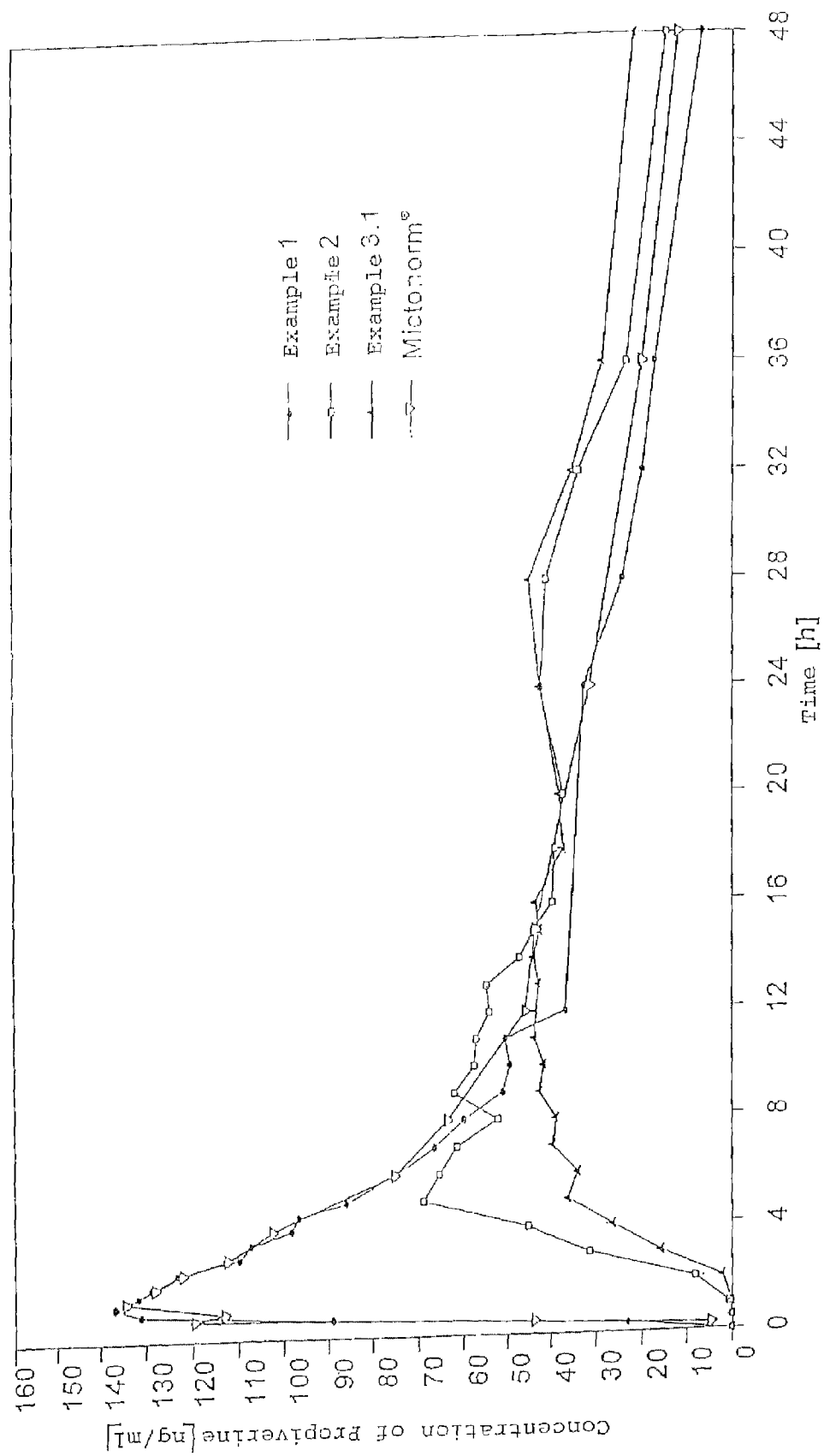
FIG. 1 plots the mean blood level value of propiverine over time after administration of several invention formulations versus a comparative commercial product, as described in Example 14.

The preferred embodiments have generally in common that, apart from 4-60 mg propiverine, preferably 9-45 mg propiverine or the equivalent amount of pharmaceutically acceptable salts thereof, and optionally an acidic substance having a $pK_a$ value of less than 6.65, preferably of 1.8 to 6.5, is included, and these two components are coated with one or more retarding (controlled releasing) layers, comprising a material insoluble in gastric fluid and insoluble in intestinal fluid and/or a material insoluble in gastric fluid and soluble in intestinal fluid, and/or are embedded in a controlled release matrix, which includes a swellable or insoluble material and which may optionally be coated with a material which is insoluble in gastric fluid and soluble or insoluble in intestinal fluid, respectively.

Oral dosage forms according to the invention can, however, also be realized without the addition of an acidic substance, on principle.

Apart from the active agent, the preferred inventive compositions include at least one pharmaceutically acceptable organic or inorganic acid having a $pK_a$ value of less than 6.65, in particular edible organic acids and pharmaceutically acceptable salts of multi-basic acids, for example citric acid, tartaric acid, succinic acid, adipic acid, ascorbic acid, fumaric acid, sodium or potassium hydrogentartrate, sodium or potassium dihydrogencitrate, di-sodium or di-potassium hydrogencitrate etc., or mixtures of these acids and salts in a ratio of 2:1 to 20:1, preferably of 3:1 to 10:1, referring to the molar equivalent ratio between the total amount of a monovalent acidic substance to propiverine or propiverine salt.

The addition of acid does not serve for the pH controlled release here but instead realises the pH independent solubility of propiverine and the salts thereof by forming a "quasi-ionpair" of propiverine and acid, leading to a sufficient release in the whole intestinal tract, independent from the kind of the propiverine salt present, for example also of salts of strong acids, like the hydrochloride. With the addition of the acid an over-saturated or concentrated aqueous drug solution of propiverine, respectively, is avoided which would lead to an immediate precipitation of the insoluble propiverine base at pH values of more than 7. Furthermore, because of its diffusion pressure the formed ionpair produces an optimal release from the retarded particles and results in an additional "protection" of the propiverine against too strong N-oxidation by protonation and probably in an improved resorption behaviour of the physiologically self-adjusting equilibrium between the resorbable free propiverine base and the less resorbable protonated form, which can be seen from the small standard deviations of the pharmacokinetic data of the inventive forms compared to the rapidly releasing commercial form.

The pH dependent or pH independent retarding, film-forming, matrix forming materials or the materials used in release modifying systems are generally known to the person skilled in the art and are commercially available, for example:

- Polymers and copolymers of acrylic and/or methacrylic acid esters, like Eudragit®, of vinylacetates and vinylpyrrolidones, like Kollidon® VA 64
- Cellulose ethers and cellulose esters, like Methocel® and Aquacoat® and Tylose®
- Alginates, like Kelacid®, Texamid®
- Xanthanes, like Keltrol®, Rhodigel®, further polysaccharides or modified polysaccharides, like Chitosan, Guargum and Gum arabicum
- Polyvinylalcohols, like Mowiol®
- Cellulose acetate phthalates, like Aquateric®
- Mono-, di- and triglycerides, like Cutina®
- Waxes, like montaneglycolwax—HOECHST or resins, like shellac
- Proteins and modified proteins The use of acidic adjuvants according to the invention in combination with retarding coatings and/or a retardant (controlled release) matrix allows the production of so-called multiple-unit formulations as well as of so-called single-unit formulations.

So-called multiple-unit formulations in the form of pellets are a particularly preferred embodiment.

According to the invention these pellets can have a particle size of 0.1 to 2.5 mm, preferably 0.6 to 1.5 mm, and can then be filled into capsules or sachets or can be compacted together with tabletting adjuvants into tablets, whereby these spheroid particles can be included in same or different sizes in one formulation.

By combination of several technology steps spheroid particles of acidic substances having a diameter of 0.1 to 2.0 mm, preferably of 0.5 to 1.2 mm, are firstly prepared in a known manner, for examples particles of crystalline citric acid, tartaric acid etc., by use of a fluidized be method from suspensions consisting of adjuvants, like lactose, of dissolved acids, like for example citric acid, of binders, like for example polyvinylpyrrolidone, and of anti-adhesive agents, like for example talcum.

In order to control the dissolution of the highly water-soluble edible acids or of the other acidic substances the rounded acid cores according to the invention are coated with a lacquer film, for example in a fluidised bed.

The materials of the gastric fluid insoluble and pH dependent intestinal fluid soluble membranes, like Eudragit® S and Eudragit® L are commonly known. The same is true for the optional addition of binders or plasticisers, like polyvinylpyrrolidone or triethylcitrate.

It could not be foreseen that in the case of propiverine or the salts thereof such a lacquer film is extraordinarily advantageous for the inventive forms. If this lacquer film is missing the diffusion caused by a high diffusion pressure and being unhindered may result in an undesirable rapid release of propiverine even despite the retarding of the active agent containing particles and the subsequent gastric fluid resistant retarding of these particles, and may lead to a significantly decreased amount of propiverine released in the further release behaviour caused by a premature depletion of the acid reservoir (Embodiment Example 7).

In the next technological step propiverine or one of the salts thereof is applied in an amount as necessary in a principally known manner, for example in a fluidised bed, together with the addition of adjuvants, adhesives and binders and further portions of the already mentioned acids or acidic substances in an alcoholic aqueous suspension. There is also the possibility to apply a microns active agent with or without the addition of microcrystalline adjuvants and the acids or acidic substances as mentioned in powderform, after a previous spraying of the retarded acid cores with an adhesive solution. The addition of portions of the same or different acids in relation to the acid being present in the coated acid core is advantageous in order to obtain an initial dissolution/release by buffering the intestinal fluid penetrating through the subsequent retarded coating.

For the inventive composition with a delayed release which is controlled until its end it is favourable to coat the retarded acid core loaded with the active agent in a next technological step, with one or more retardation (controlled release) coatings individually or as a combined mixture with our without a further addition of binders and adjuvants.

The gastric fluid insoluble, pH independent intestinal fluid insoluble materials to be used according to the invention having varying high permeability and the gastric fluid insoluble, pH dependent intestinal fluid soluble materials are commercially available, for example Eudragit® RS, Eudragit® RL and Eudragit® S or Eudragit® L, respectively.

The optimum amounts of the individual components, for example the composition of the corresponding mixtures depend on several factors, like for example the desired retarding effect, the kind of the individual retarding components having their specific solubility and permeability, and the ratio of acidic substance to active agent propiverine.

These parameters vary completely independently from each other and are of essential importance for the controlled and long-lasting, prolonged release of the propiverine.

With the use of difficult in vitro and in vivo experiments involving a discovered in vivo/in vitro correlation these problems could be solved. With the in vivo/in vitro correlation found it is possible, without difficult clinical in vivo experiments, to prepare dosage forms of propiverine according to the invention in any composition, by a simple determination of in vitro release parameters. If the release values determined correspond to the claimed release ranges, this dosage form is clinically relevant.

It has surprisingly been found that it is favourable that in the case of propiverine the retardation coating sprayed onto the active agent containing acid cores does not dissolve in the resorbing part of the gastric and intestinal tract as long as practically the whole active agent has diffused in a time-controlled manner in the form of its acid ionpair. Advantageously this coating should retain the acid being present in the core as long as the formation of the propiverine acid ionpair has completely finished. If the coating prematurely solubilises or if it leaks too much, the gastric fluid always being present in a large excess penetrates into the interior of the particles and neutralises the acid being present there. Thus, because of the low solubility of the propiverine in the pH range of the gastric fluid practically no active agent can be dissolved and diffuse from the particles. The acid being present in the interior of the particles lowers the pH value of the penetrating intestinal fluid, and then forms the corresponding ionpair. After that the solution of the propiverine acid ionpair being formed in the interior diffuses through the membrane into the intestine. Although unfavourable pH conditions are again dominating here, obviously over-saturation phenomena occur, ensuring a sufficient resorption of the per se hardly soluble active agent. Naturally the acid being present in the particles is furthermore reduced during the course of the release so that actually a strong decrease in the diffusing amount or in the release of propiverine should occur. In order to avoid the latter the retardation coating controlling the release rate should preferably be "partially soluble" in the gastric fluid. The term "partially soluble" has to be understood in the meaning of a certain permeability or as a diffusion resistance, respectively. Further, said retardation coating should additionally guarantee that in the interior of the particles acidic pH conditions are always predominating and optionally occurring pH deviations caused by food influences or by other influences are adjusted.

Even small deviations in the ratio of Eudragit® RS/Eudragit® RL/Eudragit® S lead to drastic changes of the release profiles. If the ratio of Eudragit® RS/Eudragit® RL/Eudragit® S of 2:1:2 purely found by chance is slightly changed to a ratio of 1.5:1:2.5 (Example 9) this reduction of the intestinal fluid insoluble component with low permeability (Eudragit® RS) and the increased portion of the intestinal fluid soluble material (Eudragit® S) leads to a faster release of the active agent or to a heavy diffusion of the acidic component, respectively.

This effect may be explained as follows: Since the gastric fluid insoluble, intestinal fluid soluble material of this coating is dissolved in the intestinal fluid after a certain residence time of the particles in the intestinal fluid, a too heavy release in the upper intestinal tract is effectively suppressed with a ratio of Eudragit® RS/Eudragit® L/Eudragit® S of 2:1:2, and the release of the active agent is completely shifted to the medium and lower intestinal tracts. Thus, said retardation coating reduces the particularly rapid resorption in the upper intestinal tract without reducing the total release of the active agent from the particles. This leads indisputably to a prolongation of the release of the active agent.

In order to obtain a gastric fluid resistance and not too high initial release values in the following or to further modify the release characteristics, respectively, it is common practice in the art to apply further retardation coating with gastric fluid insoluble and intestinal fluid soluble materials, for example Eudragit® L or Eudragit® S, respectively.

Furthermore the retardation coatings used according to the invention may contain typical adjuvants, like for example plasticisers, wetting agents and anti-adhesive agents. Examples for suitable pharmacologically secure plasticisers are glycerine triacetate, polyethyleneglycols and citric acid esters, like triethylcitrate. The application of retardation coatings onto the active agent containing particles may be done with methods known per se, for example in a rapidly rotating vessel or by spraying the lacquers in fluidised bed processes.

The subsequent drying of the pellets in order to remove the residual solvents originating from the suspension is known from the prior art.

The retarded particles obtained which may be in the form of retarded pellets, granules or compacted particles may be filled into capsules or sachets, preferably hard gelatine capsules, as desired. It is possible to blend particles having different delay levels and to optionally also add non-delayed particles of the active agent as a so-called starting dose. The retarding particles may, however, be compacted together with tabletting adjuvants, like cellulose, lactose, magnesiumstearate and the like, into tablets. This is in particular possible with retarding particles having a diameter below 1 mm without substantially damaging the retardation coatings. Such a table decomposes in less than 1 minute and releases the propiverine retarding particles in their inventive form—like the hard gelatine capsule does.

A further preferred embodiment of so-called multiple-unit formulations are granules and compact particles containing one or more acidic substances apart from propiverine or one salt thereof which are not embedded in a retarding matrix, but which only include this mixture together with one or more controlled release coatings, and which are subsequently compacted into tablets.

These so-called spheroid tablet formulations are produced in that propiverine or one of the pharmaceutically acceptable salts thereof in the inventive molar ratio with one or several acidic substances is compacted under strong pressure together with spheronising agents, like for example lactose, microcrystalline cellulose, hydroxypropylcellulose, with lubricating agents, like for example magnesiumstearate, and with further adjuvants, like for example polyvinylpyrrolidone, in a microcrystalline form, for example with a particle size of less than 0.25 mm, and is then once again broken and screened to a particle size of, for example, 0.5-1.5 mm, the fine fraction is once again compacted and these technological steps are repeated as long as the total mixture of the granular particles have been transferred into the desired size.

Such granular particles may, however, also be produced by other methods, for example by extrusion/spheronisation, apart from the compacting method described.

In the following the granular particles are coated with generally known gastric fluid insoluble and intestinal fluid soluble and/or gastric fluid insoluble and intestinal fluid insoluble retarded agents, like for example Eudragit® NE, Eudragit® L etc. Generally known tabletting adjuvants, like microcrystalline cellulose, crospovidone, polyvinylpyrrolidone, magnesiumstearate etc., are added, the total blend is thoroughly mixed and pressed into tablets. Furthermore the thus produced tablets can be coated with suitable coatings, which may be release modifying. Even in this case the retardation layers guarantee the formation of a propiverine acid ionpair and its controlled diffusion. Since the inventive formulations decompose in less than 5 minutes and thereby release hundreds of retarded propiverine acid particles the decomposition time does not have any influence on the release behaviour.

In contrast to the so-called multiple-unit formulations based on pellets or spheroid particles, retarded preparations of propiverine may also be produced in any other way, for example as single-unit formulation.

In particular suitable release characteristics may be achieved by matrix retardation, for example by means of a matrix tablet.

Preferably, however, also in this embodiment one of the already mentioned acidic substances is used and the acidic substance as well as the active agent is embedded in the retarding matrix. The initially mentioned acidic substances, polymers, doses and molar ratios of acidic substance in relation to propiverine are principally suitable.

For example, for the preparation of inventive matrix tablets propiverine or one of the pharmaceutically acceptable slats thereof and optionally one or several acidic substances in a molar ratio according to the invention are intimately blended with retarding, matrix-forming adjuvants, like for example cellulose ethers, cellulose esters, alginates, xanthanes, polyvinylalcohols, fats, waxes and further tabletting adjuvants, like for example magnesiumstearate, in microcrystalline form with a particle size of preferably less than 0.25 mm and pressed into tablets. In the case of propiverine and the salts thereof it has been found that the selection of the acidic substances may be done independently from their solubility in water. Thus, for example adipic acid which is more difficult to solubilise in water and also the tartaric acid which is easier to solubilise in water result in equal release profiles when used according to the invention. When contacting these tablets with water, for example in the case of a matrix made of alkylcelluloses, a highly viscose gel layer is immediately formed which reduces the diffusion of the formed propiverine-acid-ionpair in accordance with the desired release rate.

Apart from the already described dosage form comprising propiverine, one or several acidic substances and retarding materials, there is also the possibility to delay the release of combinations of propiverine or one or several pharmaceutically acceptable salts thereof with one or more other active agents in the same manner, independent from the fact whether the used combination agents are acidic substances, like in the case of the already mentioned ascorbic acid, or not.

The invention is further illustrated by means of the following Embodiment Examples without being restricted thereto.

EMBODIMENT EXAMPLES

All percentages provided refer to percent by weight (wt.-%), unless indicated otherwise.

Example 1

Pellet Formulation with Propiverine Hydrochloride—100% Release After 15 Minutes

For the preparation of spherical citric acid cores 3.5 kg citric acid having a particle size of 0.7-1.0 mm (Roche) were sprayed at an air temperature of 45° C. using 2-substance nozzles in a fluidised bed with an isopropanolic aqueous suspension consisting of 105 g polyvinylpyrrolidone (Kollidon® K25), 35 g citric acid, 275 g lactose (Microtose®), 210 g talc, 1500 g 2-propanol and 300 g water and a total yield of 4.060 kg (98.4% of the theoretical amount, referring to the solvent-free material) of rounded citric acid pellets was obtained.

3.75 kg of said rounded citric acid pellets are retarded with an isopropanolic aqueous suspension consisting of 600 g Eudragit® S12.5 (corresponding to 75 g Eudragit® S), 600 g Eudragit® L 12.5 (corresponding to 75 g Eudragit® L), 20 g triethylcitrate, 100 g talc, 1500 g 2-propanol and 300 g water in an analogous manner in the next technology step. The total yield was 4.013 kg (99.8% of the theoretical amount, referring to solvent-free material).

For application of the active agent 3.95 kg of the retarded citric acid cores were sprayed in an analogous manner using 2-substance nozzles in the fluidised bed at 45° C. air feed temperature with an isopropanolic aqueous suspension of 1300 g of micronised propiverine hydrochloride, 280 g polyvinylpyrrolidone (Kollidon® K25), 50 g citric acid, 200 g talc, 50 g magnesiumstearate, 2100 g 2-propanol and 400 g of water. The total yield obtained was 5.772 kg of active agent containing previously retarded citric acid pellets (90% referring to solvent-free material).

The content of propiverine-hydrochloride in the pellets was determined by means of the method described in Example 6 to be 20.9% and the content of citric acid to be 59.8%. This corresponds to a molar ratio of propiverine-hydrochloride to citric acid of 1:6.0.

From the substance amounts used a molar ratio of propiverine-hydrochloride/citric acid of 1:5.2 is calculated. This difference may be explained by losses during spraying and abrasion.

For filling into capsules, 10 g of microfine talc was added to 2000 g of the obtained pellets and mixed for 15 minutes. The release data were determined by means of the method described in Example 5 and are listed in the Table provided there.

Then the material is screened and the fraction having a particle size of 0.7-1.25 mm in diameter (98.0%) is further processed. 215 mg pellets corresponding to 45 mg propiverine-hydrochloride were filled into hard gelatine capsules and were used for the bioavailability study (Example 13).

Example 2

Pellet Formulation with Propiverine Hydrochloride—50% Release After 3 Hours

For the preparation of spherical citric acid starter cores 3500 g citric acid granules (Roche) having a particle size of 0.7-1.0 mm were sprayed in a technically equivalent manner as described in Example 1 with a suspension consisting of 30 g polyvinylpyrrolidone (Kollidon®), 10 g citric acid, 70 g lactose (Microse®) and 60 g talc in 340 g 2-propanol and 75 g water in a fluidised bed. 3665 g of rounded citric acid pellets were obtained (99.7% of the theoretical amount, referring to the dry substance used)

In the next step 3660 g of the above described citric acid pellets were sprayed with a suspension consisting of 600 g Eudragit® S12.5 (75 g dry substance Eudragit® S), 600 g Eudragit L 12.5 (75 g dry substance Eudragit® L), 20 g triethylcitrate and 100 g microfine talc in 1500 g 2-propanol and 300 g water. The total yield was 3930 g corresponding to 100%, referring to solvent-free material.

3650 g of these pellets were sprayed in the above described manner with a suspension consisting of 1000 g micronised propiverine-hydrochloride, 215 g polyvinylpyrrolidone (Kollidor® K25), 40 g citric acid, 155 g microfine talc and 40 g magnesiumstearate in 2100 g 2-propanol and 310 g demineralised water. The total amount obtained was 5030 g of active agent pellets. This corresponds to a yield of 98.6%, referring to dry mass.

In a next technology step 3500 g of these active agent pellets were retarded in the fluidised bed at an air feed temperature of 40-45° C. by means of 2-substance nozzles with an isopropanolic aqueous suspension of 420 g Eudragit® RL 12.5 (corresponding to 52.5 g Eudragit® RS dry mass), 420 g Eudragit® RL 12.5 (corresponding to 48.4 g Eudragit RL dry mass), 560 g Eudragit® S 12.5 (corresponding to 75 g Eudragit® S dry mass), 20 g triethylcitrate, 120 g talcum, 1400 g 2-propanol and 210 water, and were dried intensively in the fluidised bed. The total yield obtained was 3815 g (100% of the theoretical amount, referring to solvent-free material).

In the next step a suspension of 1392 g Eudragit® L 12.5, 16 g triethylcitrate and 105 g microfine talc in 1135 g 2-propanol and 380 g water were applied onto 2900 g of the retarded active agent pellets. The total amount obtained was 3190 g pellets (99.8% of the theoretical yield, referring to dry mass).

For further retardation of the pellets a suspension of 300 g Eudragit® RL 12.5 (37.5 g dry mass), 4 g triethylcitrate, 35 microfine talc and 96.5 g magnesiumstearate in 1370 g 2-propanol and 340 g water was then applied onto 2500 g of the retarded active agent pellets. The total amount obtained was 2585 g pellets corresponding to a yield of 99.5% of the theoretical amount, referring to the dry mass.

Before filling into capsules 2500 g pellets were mixed with 12.5 microfine talc for 15 minutes and subsequently screened. 2425 g (96.5%) of the pellets have a particle size of 0.7-1.25 mm in diameter.

The content of propiverine-hydrochloride in the pellets was determined according to the method described in Example 6 to be 13.7%.

The content of citric acid in said pellets was also determined according to the method described in Example 6 to be 53.0%. This corresponds to a molar ratio of propiverine-hydrochloride citric acid of 1:8.1.

From the substance amounts used, a molar ratio of propiverine-hydrochloride to citric acid of 1:6.9 was calculated. This difference may also be explained by losses during spraying and losses through abrasion.

For the bioavailability study of Example 14, 328 mg pellets corresponding to 45 mg propiverine-hydrochloride are filled into hard gelatine capsules. The release data were determined according to the method described in Example 5 and are listed in the Table provided there.

Example 3

Pellet Formulation with Propiverine Hydrochloride—About 20% Release After 3 Hours and About 80% Release After 10 Hours Example 3.1

Batch Size on a Technical Scale

In the same manner, the same batch size and in the same composition of substances as described in Example 1, once again 5638 g (96.7% of the theoretical amount, referring to solvent-free material) of propiverine-hydrochloride containing previously retarded citric acid pellets were obtained.

2900 g of the above described active agent pellets were sprayed with a suspension of 600 g Eudragit® RS 12.5 (75 g dry substance Eudragit® RS), 304 g Eudragit® RL 12.5 (38 g dry substance Eudragit® RL), 600 g Eudragit® S 12.5 (75 g dry substance Eudragit® S), 20 g triethylcitrate and 120 g microfine talc in 1415 g 2-propanol and 220 g demineralised water. The total amount was 3227 g retarded active agent pellets (corresponding to 100% of the theoretical yield, referring to solvent-free material).

3100 g of these pellets were then sprayed with a suspension consisting of 868 g Eudragit® S 12.5 (108.5 g Eudragit® S dry mass), 11 g triethylcitrate, 65 microfine talc, 840 g 2-propanol and 100 g water. The total amount of pellets was 3285 g corresponding to 100% of the theoretical amount, referring to solvent-free pellets.

Before filling into capsules, 3200 g of the thus obtained pellets were mixed with additional 16 g of microfine talc for 15 minutes and then screened. The particle size fraction of 0.7 mm to 1.25 mm (3120 g, corresponding to 97% of the theoretical amount) shows an experimentally determined content of 18.8% propiverine-hydrochloride.

The content of citric acid in the pellets was determined by means of the potentiometric titration as described in Example 6 to be 50.7%.

From the amounts experimentally determined follows a molar ratio of active agent to citric acid of 1:5.7.

The theoretical ratio calculated on the basis of the masses used is 1:5.2. The difference may also be explained by losses during spraying and losses through abrasion.

240 mg of the above described pellets corresponding to 45 mg propiverine-hydrochloride were filled into hard gelatine capsules and were used for the bioavailability study of Example 14.

The release data were determined according to the method described in Example 5 and are listed in the table provided there.

Example 3:2

Batch Size in a Scale Relevant for Production

For the manufacture of citric acid cores as starter pellets 250.0 kg citric acid granules (Roche) having a particle size between 0.7 mm and 1.0 mm were sprayed by means of 2-substance nozzles in the fluidised bed with a suspension of 7.5 kg polyvinylpyrrolidone (Kollidon® K25), 2.5 kg citric acid, 19.6 kg lactose and 15.0 kg microfine talc in 89.3 kg 2-propanol and 19.6 kg demineralised water. By this method 282.0 kg spherical citric acid starter cores were obtained (95.7% of the theoretical amount, referring to solvent-free material).

200.0 kg of these starter cores were then sprayed in a technically equivalent manner with a suspension of 4.0 kg Eudragit® S100, 4.0 kg Eudragit L100, 1.1 kg triethylcitrate and 5.3 kg microfine talc in 94.0 kg 2-propanol and 11.0 kg demineralised water. The total amount obtained was 214.0 kg corresponding to 99.8% of the theoretical amount, referring to the dry mass used.

Through subsequent screening all pellets having a diameter of less than 1.25 mm were isolated.

In the following technology step the thus obtained retarded starter cores were sprayed in two steps with a suspension of 85.3 kg propiverine-hydrochloride, 22.7 kg polyvinylpyrrolidone (Kollidon® K25), 8.5 kg citric acid, 11.1 kg microfine talc, 0.802 kg magnesiumstearate, 165.5 kg 2-propanol and 48.2 kg demineralised water. The yield in both steps was 94.8%, referring to the dry mass used.

243.0 kg of the active agent pellets thus obtained having an amount of 21.75% propiverine-hydrochloride were coated for purposes of retardation in a fluidised bed with a suspension of 54.7 kg Eudragit® RS 12.5 (6.7 kg Eudragit® RS dry substance), 27.8 kg Eudragit RL (3.4 kg Eudragit® RL dry substance), 6.7 kg Eudragit® S100, 1.8 kg triethylcitrate and 10.8 kg microfine talc in 207.3 kg 2-propanol and 23.8 kg demineralised water. The yield was 99.2% of the theoretical amount of solvent-free retarded particles.

237.4 kg of the above described retarded active agent pellets were coated in a fluidised bed with a suspension of 5.7 kg Eudragit® S100, 0.582 kg triethylcitrate and 3.5 kg microfine talcum in 44.6 kg 2-propanol and 5.4 kg demineralised water.

The pellets were dried for 60 hours at 70° C. before filling into capsules. 13.0 kg of the pellets were then mixed with 65 g talcum for 10 minutes and subsequently screened over a 1.25 mm screen. 12.8 kg of said pellet fraction having a particle size of less than 1.25 mm showed a content of 18.8% of propiverine-hydrochloride and 49.8% of citric acid, determined according to the method described in Example 6. The molar ratio of active agent to citric acid was 1:5.6.

240 mg of the thus obtained pellets each, corresponding to 45 mg propiverine-hydrochloride were filled into hard gelatine capsules and used for the bioequivalence study of Example 15.

The release of propiverine from the pellets was carried out under the conditions as described in Example 5. The results are listed in the Table provided there.

Example 4

Pellet Formulation with Propiverine 2400 g spherical citric acid cores which were produced in the same manner as already described in Example 3.2 were coated in a fluidised bed at an air feed temperature of 40-74° C. with a suspension consisting of 48 g Eudragit® S100, 48 g Eudragit L100, 13 g triethylcitrate, 65 g microfine talcum, 1860 g isopropanol and 200 g water.

2500 g of the thus obtained retarded starter cores were sprayed under the same technical conditions with a suspension of 828 g propiverine base, 177 g polyvinylpyrrolidone (Kollidon® K25), 63 g citric acid, 200 g microfine talcum and 32 g magnesiumstearate in 3100 g 2-propanol and 400 g water. The total amount obtained was 3740 g active agent pellets corresponding to 98.4% of the theoretical amount, referring to the dry substance used.

In the same manner 3250 g of the active agent pellets were sprayed with a suspension of 720 g Eudragit® RL 12.5 (90 g dry mass Eudragit® RS), 368 g Eudragit® RL 12.5 (46 g Eudragit® RL dry mass), 90 g Eudragit® S100, 24 g triethylcitrate and 146 g microfine talcum in 1930 g 2-propanol and 300 g demineralised water.

3500 g of thus obtained retarded active agent pellets were sprayed in the fluidised bed under identical conditions with a suspension consisting of 86 g Eudragit® S100, 9 g triethylcitrate, 52 g microfine talcum, 129.9 g 2-propanol and 80 g water.

The thus obtained pellets showed a content of 19.4% propiverine as well as a content of 40.4% citric acid as determined by the methods described in Example 6. This results in a molar ratio of active agent to citric acid of 1:4.0.

The release of propiverine from the pellets was determined by the method described in Example 5 and is indicated in the Table provided there.

Example 5

Determination of the Release Data—Comparison of the Release Data of Examples 1-4, 7-13

The determination of the release of propiverine-hydrochloride or propiverine, respectively, from all of the described oral dosage forms was made with the help of the basket apparatus as described in Ph. Eur. 3, 2.93 at 100 rpm for 17 hours.

For this an amount of pellets corresponding to 45 mg propiverine-hydrochloride each was weighed into 6 baskets. The release is carried out for one hour in 750 ml gastric fluid medium (0.1 M hydrochloric acid solution) at 37° C. This medium is thrown away after measurement of the 1 hour value and the release is then carried out in 750 ml of an 50 mM potassium dihydrogenphosphate buffer at pH 5.8 at 37° C. for further 16 hours.

The quantification of propiverine-hydrochloride or propiverine, respectively, in the release medium is carried out by means of an on-line coupled UV/VIS-spectrophotometer. For the measurement the release medium is pumped at predefined periods from each release container through polypropylen filters via a 6-channel tube pump into the flow vessel of the UV/VIS-spectrophotometer. The measurement of the extinction is at 239 nm whereby the extinction at 247 nm is additionally determined as the background. For calculation of the amount of propiverine-hydrochloride/propiverine the extinction value at the background wavelength is subtracted from the extinction value at the measurement wavelength.

The calculation of the release data is carried out in relation to one sample of a reference substance which is measured under the same conditions in the UV/VIS-spectrometer. The amount of propiverine-hydrochloride or propiverine, respectively, which is released during the first hour in 0.1 M hydrochloric acid is added to the further release values.

The release data obtained are shown in Tables 1 and 2 as the mean values of a six fold determination.

| | Tabelle 1: Release of propiverine-hydrochloride/propiverine in percent— Examples 1-4(n.d.—not determined) | | | | |
|---|---|---|---|---|---|
| Time [h] | Example 1 (pellet) Propiverine-hydrochloride-100% after 15 min | Example 2 (Pellet) Propiverine-hydrochloride-50% after 3 h | Example 3.1 (Pellet) Propiverine-hydrochloride-20% after 3 h, 80% after 10 h | Example 3.2 (Pellet) Propiverine-hydrochloride-20% after 3 h 80% after 10 h | Example 4 (Pellet) Propiverine-20% after 3 h 70% after 10 h |
| 0.08 | 103.06 | n.d. | n.d. | n.d. | n.d. |
| 0.17 | 101.41 | n.d. | nd. | n.d. | n.d. |
| 0.25 | 100.05 | n.d. | nd. | n.d. | n.d. |
| 0.5 | n.d. | 0.43 | 0.00 | 0.69 | 0.59 |
| 1 | 101.08 | 6.41 | 0.85 | 1.00 | 2.76 |
| 1.5 | — | 14.75 | 4.70 | 1.38 | 7.57 |
| 2 | — | 23.92 | 10.01 | 5.26 | 13.01 |
| 3 | — | 42.07 | 22.65 | 20.61 | 23.64 |
| 4 | — | 57.78 | 35.87 | 33.37 | 32.80 |
| 5 | — | 70.11 | 48.18 | 44.82 | 41.13 |
| 6 | — | 79.16 | 58.83 | 55.28 | 48.49 |
| 7 | — | 85.44 | 67.55 | 64.15 | 54.84 |
| 8 | — | 89.62 | 74.38 | 71.03 | 60.66 |
| 9 | — | 92.29 | 79.53 | 76.16 | 65.48 |
| 10 | — | 93.94 | 83.29 | 79.88 | 69.73 |
| 11 | — | 94.93 | 85.96 | 82.50 | 72.95 |
| 12 | — | 95.51 | 87.80 | 84.58 | 75.78 |

Tabelle 1: Release of propiverine-hydrochloride/propiverine in percent—
Examples 1-4(n.d.—not determined)

| Time [h] | Example 1 (pellet) Propiverine-hydrochloride-100% after 15 min | Example 2 (Pellet) Propiverine-hydrochloride-50% after 3 h | Example 3.1 (Pellet) Propiverine-hydrochloride-20% after 3 h, 80% after 10 h | Example 3.2 (Pellet) Propiverine-hydrochloride-20% after 3 h 80% after 10 h | Example 4 (Pellet) Propiverine-20% after 3 h 70% after 10 h |
|---|---|---|---|---|---|
| 13 | — | 95.83 | 89.03 | 86.22 | 78.33 |
| 14 | — | 96.01 | 89.84 | 87.42 | 79.89 |
| 15 | — | 96.11 | 90.36 | 88.44 | 81.81 |
| 16 | — | 96.16 | 90.69 | 89.33 | 83.05 |
| 17 | — | 96.19 | 90.89 | 90.04 | 85.78 |

Tabelle 2: Release of propiverine-hydrochloride/propiverine in percent—
Examples 7-12 (n.d.—not determined)

| Time [h] | Example 7 (Pellet) Propiverine-HCl, non-retarded citric acid cores | Example 8 (Pellet) Propiverine-HCl citric acid 1:12 | Example 9 (Pellet) Propiverine-HCl, tablets) Eudragit RS/RL/S 1,5:1:2,5 | Example 10 (Spheroidal tablets) Propiverine-HCl, citric acid | Example 11 (gel matrix tablets) Propiverine-HCl, tartaric acid | Example 12 (gel matrix tablets) Propiverine-HCl, adipic acid | Example 13 (gel matrix tablets) without acid |
|---|---|---|---|---|---|---|---|
| 0.08 | n.d. | n.d. | n.d. | n.d. | n.d. | n.d. | n.d. |
| 0.17 | n.d. | n.d. | n.d. | n.d. | n.d. | n.d. | n.d. |
| 0.25 | n.d. | n.d. | n.d. | n.d. | n.d. | n.d. | n.d. |
| 0.5 | 0.30 | 0.00 | 0.52 | 0.35 | 2.69 | 0.16 | 4.64 |
| 1 | 0.56 | 0.00 | 1.47 | 1.80 | 6.17 | 5.12 | 9.55 |
| 1.5 | 5.58 | 3.41 | 10.48 | 3.26 | 11.08 | 10.66 | 15.63 |
| 2 | 17.42 | 8.80 | 28.60 | 6.41 | 14.54 | 14.61 | 20.38 |
| 3 | 37.14 | 35.46 | 48.91 | 16.54 | 20.96 | 21.75 | 27.99 |
| 4 | 55.53 | 59.52 | 67.24 | 26.82 | 26.92 | 28.23 | 34.34 |
| 5 | 63.46 | 78.80 | 78.84 | 38.45 | 32.43 | 34.29 | 39.52 |
| 6 | 68.17 | 83.27 | 83.36 | 49.61 | 37.57 | 39.91 | 44.19 |
| 7 | 71.00 | 87.54 | 84.00 | 59.24 | 42.30 | 45.03 | 48.25 |
| 8 | 73.81 | 90.13 | 84.82 | 65.53 | 46.75 | 49.95 | 52.14 |
| 9 | 75.90 | 91.38 | 85.56 | 71.55 | 50.94 | 54.47 | 55.71 |
| 10 | 77.48 | 91.72 | 86.22 | 75.12 | 54.80 | 58.74 | 58.70 |
| 11 | 77.81 | 92.01 | 86.90 | 77.83 | 58.33 | 62.73 | 61.81 |
| 12 | 78.26 | 92.42 | 87.72 | 80.67 | 61.61 | 66.14 | 64.65 |
| 13 | 78.65 | 92.76 | 88.41 | 82.98 | 64.75 | 69.42 | 67.34 |
| 14 | 79.00 | 93.10 | 89.19 | 84.82 | 67.61 | 72.58 | 69.71 |
| 15 | 79.46 | 93.51 | 89.75 | 85.36 | 70.36 | 75.44 | 72.06 |
| 16 | 79.81 | 93.94 | 89.93 | 86.16 | 72.91 | 79.99 | 74.14 |
| 17 | 80.20 | 94.32 | 90.26 | 86.40 | 75.33 | 80.49 | 76.74 |

Example 6

Determination of the Amount of Propiverine/Propiverine-Hydrochloride via HPLC and of Citric Acid Via Potentiometric Titration and of 2-propanol via GC 1. For a quantitative determination of propiverine/propiverine-hydrochloride in varying dosage forms a drug-specific HPLC method is used which allows to separate matrix components from analytes.

The method used provides correct results since it is valid with respect to its selectivity for the analyte, linearity in the predetermined working range, correctness and precision, which could be shown by means of the above commonly known experiments.

For a quantitative determination of propiverine/propiverine-hydrochloride in the active agent containing dosage forms, for example an amount of the finely powdered dosage form corresponding to 15.0 mg propiverine-hydrochloride is exactly weighed into a 100 ml volumetric flask, mixed with 50 ml of methanol and one drop of 0.1 M hydrochloric acid and then treated in an ultrasonic bath for about 10 minutes. Then 40 ml water were added and the suspension is once again treated for about 10 minutes in an ultrasonic bath. After cooling down to room temperature water is added up to the calibration mark.

As the reference solution, 60.0 mg propiverine-hydrochloride are exactly weighed into a 100 ml volumetric flask, mixed with 50 ml of methanol and one drop of 0.1 M hydrochloric acid and then treated in an ultrasonic bath for about 10 minutes. Then 40 ml of water are added and the solution is once again treated in the ultrasonic bath for about 10 minutes. After cooling down to room temperature water is added up to the calibration mark.

The chromatography is then carried out with a commercial apparatus consisting of a pump, an autosampler, a column oven and a UV/VIS detector, at a flow rate of 1.0 ml/min, 40° C. column temperature and a detection wavelength of 220 nm, whereby the running time is 5 minutes and the amount of injected sample or reference solution, respectively, is 20 µl. As a stationary phase a reversed phase material (LiChrospher 60 Select B, 5 µm, 125×4 mm, from Merck) and a mobile phase consisting of 56 parts per volume of a 10 mM potassium dihydrogenphosphate buffer, pH 1.0 (with 85% phosphoric acid) and 44 parts per volume of acetonitrile are used.

The quantification of propiverine/propiverine-hydrochloride in the sample is carried out as a double determination against the corresponding peak in the chromatogram of the reference solution at the same wavelength. The result is given in weight percent in the dosage form.

2. The quantitative determination of citric acid in the various dosage forms is carried out by potentiometric titration of the first equivalence point of citric acid.

The method used has been validated with respect to its specificity, correctness and precision, whereby it could be shown that adjuvants or propiverine-hydrochloride do not distort the result.

For carrying out the measurement 50.0 mg of the finely powdered dosage form were exactly weighed, mixed with 50 ml of demineralised water and then treated for about 5 minutes in an ultrasonic bath. Then it was titrated to the first equivalence point with 0.1 M sodium hydroxide solution.

1 ml of sodium hydroxide solution consumed corresponds to 6.403 mg citric acid.

3. The quantitative determination of 2-propanol in the pellet formulations is carried out via gaschromatography. This method provides correct results since it is valid with respect to its electivity for the analytes, the linearity in the predetermined working range, the correctness and the precision, which could be shown with commonly known experiments.

For determination of 2-propanol in the pellet formulations, 100 mg of each form were weighed into different centrifuge tubes and 1.0 ml of dimethylformamide was added. Then the suspension was extracted for 2 minutes in the ultrasonic bath, centrifuged for 3 minutes at 10,000 rpm and the solution was decanted into vials.

As a reference solution 100 mg of 2-propanol are weighed into a 100 ml volumetric flask and filled up to 100 ml with dimethylformamide. 2.5 ml of this solution are filled up to 50 ml with dimethylformamide (500 ppm, referring to the pellet mass in the sample solution).

The chromatography is conducted with a commonly used commercial gaschromatography apparatus having a split injection device, a temperature-adjustable column oven and a flame ionisation detector, and which is operated with helium as the carrier gas.

As the stationary phase for example a BTR-CW-column of 10 m length, an inner diameter of 0.53 mm and a film thickness of 1.0 µm is used. At a column flow of 6 ml/min, an injection volume of 1 µl and a column temperature of 60° C. 2-propanol is eluated after about 0.6 minutes.

The quantification of 2-propanol in the sample is done as a double determination against the corresponding peak in the chromatogram of the reference solution. The result is given in ppm in the dosage form.

Example 7

Retardation of Citric Acid Spheroids

In the same manner as already described in Example 1 and with the same batch size, 3990 g (corresponding to 96.7% of the theoretical amount, referring to solvent-free material) of spherical citric acid cores are obtained.

For application of the active agent, 3650 g of the non-retarded spherical citric acid cores are sprayed at an air temperature of 45° C. by means of 2-substance nozzles in a fluidised bed with an isopropanolic aqueous suspension consisting of 1200 g propiverine-hydrochloride, 260 g polyvinylpyrrolidone (Kollidon® K25), 45 g citric acid, 185 g talc, 45 g magnesiumstearate, 1940 g 2-propanol and 370 g demineralised water. The total yield obtained was 5250 g of an active agent containing non-retarded citric acid pellets (97.5%, referring to solvent-free material).

In the next technology step 3500 g of the thus obtained active agent pellets were sprayed in the fluidised bed at an air feed temperature of 40-45° C. by means of 2-substance nozzles with an isopropanolic aqueous suspension of 720 g Eudragit® RS 12.5 (90 g Eudragit® RS), 365 g Eudragit® RL 12.5 (corresponding to 45 g Eudragit® RL dry substance), 720 g Eudragit® S 12.5 (90 g Eudragit® S dry substance), 24 g triethylcitrate and 144 g microfine talc in 1700 g 2-propanol and 264 g water. The total amount obtained was 3700 g retarded active agent pellets. This corresponds to a theoretical yield of 95.0%, referring to the dry material.

2800 g of the thus obtained pellets were sprayed under identical technological conditions with a suspension of 781 g Eudragit® S 12.5 (corresponding to 98 g Eudragit® S dry substance), 100 g triethylcitrate and 58.5 microfine talcum in 760 g 2-propanol and 90 g water. The total amount of pellets obtained was 2960 g. This corresponds to a yield of 100% of the theoretical amount, referring to solvent-free pellets.

Before filling into capsules, 2900 g of the thus obtained pellets were mixed with 15 g talc and then screened. The particle size fraction of 0.7 mm to 1.25 mm (2650 g, corresponding to 91% of the theoretical amount) shows a content of 19.0% propiverine-hydrochloride as determined according to Example 5. The content of citric acid was determined according to the titration as described in Example 6 to be 53%.

The result from the experimentally determined amounts is a molar ratio of active agent to citric acid of 1:5.8.

The release of propiverine-hydrochloride from the above described pellets was determined by means of the method as illustrated in Example 5. The results are listed in the Table provided there.

Example 8

Pellet Formulation with
Propiverine-Hydrochloride—Molar Ratio of Active
Agent to Citric Acid 1:12

In the same manner as already described in Example 1 and with the same batch size 4019 g (corresponding to 97.4% of the theoretical amount, referring to dried substance) spherical citric acid cores are obtained.

3750 g of the thus obtained cores are retarded in the same manner as already described in Example 1 with an isopropanolic aqueous suspension consisting of 600 g Eudragit® S 12.5 (corresponding to 75 g Eudragit® S), 600 g Eudragit® L 12.5 (corresponding to 75 g Eudragit® L), 20 g triethylcitrate, 100 g talc, 1500 g 2-propanol and 300 g water. The total yield was 4000 g, corresponding to 99.5% of the theoretical amount, referring to solvent-free material.

3500 g of the thus obtained retarded citric acid spheroids are sprayed by means of 2-substance nozzles in the fluidised bed at 45° C. air feed temperature with an isopropanolic aqueous suspension of 575 g propiverine-hydrochloride, 250 g polyvinylpyrrolidone (Kollidon® K25), 45 g citric acid, 175 g talc, 45 g magnesiumstearate, 1860 g 2-propanol and 350 g water. The total yield obtained was 4490 g of active agent pellets (corresponding to 97.8%, referring to solvent-free material).

3500 g of the thus obtained active agent pellets were sprayed under identical technological conditions with an isopropanolic aqueous suspension consisting of 720 g Eudragit® RS 12.5 (corresponding to 90 g dry substance Eudragit® RS), 365 g Eudragit® RL 12.5 (corresponding to 45 g Eudragit® RL dry substance), 720 g Eudragit® S 12.5 (corresponding to 990 g Eudragit® S dry substance), 24 g triethylcitrate and 144 g microfine talc in 1700 g 2-propanol and 264 g water (demineralised). The total amount obtained was 3894 g of the retarded active agent pellets. This corresponds to a total yield of 100.0% of the theoretical amount, referring to the dry substance.

3100 g of the thus obtained retarded active agent pellets were then sprayed in the same manner with a suspension of 865 g Eudragit® S 12.5 (108 g Eudragit® S dry substance), 110 g triethylcitrate, 65 g talc in 840 g 2-propanol and 100 g water. 3380 g of the double-coated active agent pellets were obtained (99.9% of the theoretical amount, referring to solvent-free material).

Before filling in hard gelatine capsules, 30000 g of the thus obtained pellets were mixed under addition of 15 g talc and subsequently screened. The particle size fraction of 0.7 mm to 1.25 mm (2750 g, corresponding to 91.7% of the theoretical amount) shows a content amount of 9.8% of propiverine-hydrochloride as determined according to Example 6. The content of citric acid was determined by means of the titration as described in Example 6 to be 55.2%. This results in a molar ratio of active agent to citric acid of 1:11.8.

The release of propiverine-hydrochloride from the above described pellets was determined according to the method as illustrated in Example 5. The results are listed in the Table provided there and show that the release of the active agent is considerably reduced in the first and second hour, similar to Example 3.1. In the further course the higher amount of citric acid becomes, however, apparent, which results in a higher osmotic pressure and thus in a more rapid release of the active agent.

Example 9

Pellet Formulation with Propiverine-Hydrochloride—Eudragit Ratio RS/RL/S 1.5:1:2.5

In the same manner as already described in Example 1 and with the same batch size, 4000 g (corresponding to 97.0% of the theoretical amount, referring to solvent-free material) spherical citric acid cores are obtained.

For retardation, 3750 g of the thus obtained starter cores are sprayed in the same manner with a suspension having the same quantitative composition as already described in Example 1. The total amount of retarded citric acid cores was 3980 g which corresponds to a yield of 99.0%, referring to solvent-free material.

3500 g of the thus obtained retarded citric acid spheroids are sprayed by means of 2-substance nozzles in the fluidised bed at 45° C. air feed temperature with an isopropanolic aqueous suspension of 1100 g propiverine-hydrochloride, 250 g polyvinylpyrrolidone (Kollidon® K25), 45 g citric acid, 125 g talc, 45 g magnesiumstearate, 1860 g 2-propanol and 350 g water. The yield obtained was 4490 g of active agent pellets (corresponding to 97.8%, referring to solvent-free material).

4000 g of the thus obtained active agent pellets were sprayed under identical technological conditions with an isopropanolic aqueous suspension consisting of 615 g Eudragit® RS 12.5 (corresponding to 77 g Eudragit® RS dry substance), 410 g Eudragit® RL 12.5 (corresponding to 51 g Eudragit® RL dry substance), 1025 g Eudragit® S 12.5 (corresponding to 128 g Eudragit® S dry substance), 27 g triethylcitrate and 165 g microfine talc in 1950 g 2-propanol and 300 g water (demineralised). The total amount obtained was 4440 g of the retarded active agent pellets. This corresponds to a total yield of 99.8% of the theoretical amount, referring to the dried substance.

3100 g of the thus obtained retarded active agent pellets were sprayed in the same manner and with the same suspension as already described in Example 8. Thereby 3100 g of the lacquered active agent pellets (91.5% yield of the theoretical amount, referring to solvent-free material).

Before filling into hard gelatine capsules, 2500 g of the thus obtained lacquered active agent pellets were screened under addition of 15 g microfine talc. The particle size fraction of 0.7 mm to 1.25 mm (2450 g, corresponding to 98.0% of the theoretical amount) has a content of 18.5% of propiverine-hydrochloride as determined according to Example 6. The content of citric acid was determined by means of the titration as described in Example 6 to be 49%. Thus the result is a molar ratio of propiverine to citric acid of 1:5.6, which is in the typical range.

The release of propiverine-hydrochloride from the above described lacquered pellets was determined according to the method illustrated in Example 5. The results of the release are also to be found there.

Example 10

Spheroid Table Formulation with Propiverine-Hydrochloride

For manufacturing a tablet from gastric fluid resistant spheroidal particles 1.25 kg propiverin hydrochloride (particle size less than 0.25 mm), 2.97 kg citric acid (particle size less than 0.25 mm), 0.80 kg polyvinylpyrrolidone (Kollidon® K25), 1.44 kg lactose (Tablettose®) were mixed for 5 minutes in a double twist blender (Rhoenrad-blender). In order to clash agglomerates the mixture was put on a sieve with a mesh diameter of 0.81 mm and mixed for additional 5 minutes. The 0.05 kg of magnesiumstearate was added to this mixture via a screen having a mesh size of 0.5 mm and the total mass was mixed for further 2 minutes. The mixture has a molar ratio of propiverine hydrochloride to citric acid of 1:5.

The thus obtained mixture was compacted and the obtained particles were subsequently broken. The fraction of 0.6-1.2 mm was screened. The resulting fine fraction was repeatedly compacted, broken and screened until the total amount was present in granule particles of the size mentioned. The total yield was 5.28 kg, corresponding to 81.1% of the theoretical amount.

3.5 kg of the obtained granule particles were sprayed in the fluidised bed with an aqueous suspension of 967 g Eudragit® NE 30 D (corresponding to 290 g dry mass), 467 g Eudragit® L 30D (corresponding to 140 g dry mass), 100 g talcum and 3300 g water with a 2-substance nozzle at an air feed temperature of 50° C. and subsequently dried at an air feed temperature of 40° C. at a reduced amount of air. The total yield was 3.985 kg corresponding to 93.8% of the theoretical amount, referring to solvent-free material.

3.0 kg of the thus obtained retarded particles were mixed in a double twist blender (Rhoenrad-blender) with 5.0 kg of microcrystalline cellulose (type 101), 0.52 kg polyvinylpyrrolidone (Kollidon® K25) and 1.0 kg crospovidone XL for 20 minutes. Then 0.1 kg of magnesiumstearate were added to the mixture via a screen having a mesh size of 0.50 mm and it was again mixed for 5 minutes.

The thus obtained pressed on a rotary press with an oblong stamp tool (length 19 mm, width 8.5 mm, radius of the curvature 8 mm) into tablets having a mass of 865 mg and a fracture strength of 100-140 N.

By means of the methods described in Example 6 an account of 5.2% propiverine-hydrochloride and 11.8% of citric acid was determined. This results in a molar ratio of active agent to citric acid of 1:4.8. This difference may also be explained through abrasion losses and losses during spraying within the various technology steps.

The release of propiverine-hydrochloride from the above described tablets was determined by means of the method as described in Example 5. The data found are listed in the Table provided there.

Example 11

Gel Matrix Tablet Formulation with Propiveriene-Hydrochloride and Tartaric Acid

For the manufacture of a gastric fluid resistant gel matrix tablet having propiverine-hydrochloride and tartaric acid, 132.5 g tartaric acid having a particle size of 100% less than 250 µm, 112.5 g propiverine-hydrochloride, 187.5 g hypromellose (Methocel® K100) and 62.5 of mixrocrystalline cellulose were mixed for 10 minutes in a double twist blender, put onto a sieve having a mesh diameter of 0.81 mm and again mixed for 10 minutes. One part of the blend is pre-rubbed with 5.0 g of magnesiumstearate and the resulting abrated portion is added to the rest of the premixture over a screen having a mesh size of 500 µm. Then it is mixed again for 2 minutes.

The blend thus obtained is pressed on a rotary press having an 8 mm tool (radius of the curvature 9 mm) into tablet cores with a fracture strength of 50 N-70 N and an abrasion of less than 0.5%.

350 g of the thus obtained tablet cores are sprayed in the fluidised bed by means of 2-substance nozzles with a suspension of 48 g Eudragit® L 12.5 (6.0 g Eudragit® L dry substance), 60 mg magnesiumstearate, 600 mg talcum and 600 mg triethylcitrate in 40 g 2-propanol.

335 g of the gastric fluid resistant gel matrix tablets were obtained, corresponding to a total yield of 99.4%.

The amount of propiverine-hydrochloride was determined by the method as described in Example 6 to be 22.3%. This results in a molar ratio of active agent to tartaric acid of 1:3.2. The release of propiverine-hydrochloride from the above described matrix tablets was determined by the method according to Example 5 and it is listed in the Table provided there.

Example 12

Gel Matrix Tablet Formulation with Propiverine-Hydrochloride and Adipic Acid

For the manufacture of a gastric fluid resistant gel matrix tablet with propiverine-hydrochloride and adipic acid, 132.5 g adipic acid having a particle size of 100% less than 250 µm, 112.5 g propiverine-hydrochloride, 187.5 g hypromellose (Methocel® K100) and 62.5 g of mixrocrystalline cellulose were mixed for 10 minutes in a double twist blender, put onto a sieve having a mesh diameter of 0.81 mm and again mixed for 10 minutes. One part of the blend is pre-rubbed with 5.0 g magnesiumstearate and the resulting abrated portion is added to the rest of the premixture over a screen having a mesh size of 500 µm. Then it is mixed again for 2 minutes.

The blend thus obtained is pressed on a rotary press having an 8 mm tool (radius of the curvature 9 mm) into tablet cores with a tensile strength of 50 N-70 N and an abrasion of less than 0.5%.

350 g of the thus obtained tablet cores are sprayed in the fluidised bed by means of 2-substance nozzles with a suspension of 48 g Eudragit® L 12.5 (6.0 g Eudragit® L dry substance), 60 mg magnesiumstearate, 600 mg talcum and 600 mg triethylcitrate in 40 g 2-propanol.

356 g of the gastric fluid resistant gel matrix tablets were obtained, corresponding to a total yield of 99.46%.

The content of propiverine-hydrochloride was determined by the method described in Example 6 to be 22.7%. This results in a molar ratio of active agent to adipic acid of 1:3.2. The release of propiverine-hydrochloride from the above described matrix tablets was determined according to the method described in Example 5 and it is listed in the Table provided there.

Example 13

Gel Matrix Tablet Formulation with Propiverine-Hydrochloride Without Addition of Acid For the manufacture of a modified gel matrix tablet with propiverine-hydrochloride and without acidic substances, 45 g propiverine-hydrochloride having a particle size of less than 0.25 mm, 247 g microcristalline cellulose (type 101) and 67 g hypromellose (Methocel® K100) were mixed for 10 minutes in a double twist blender, put onto a sieve having a mesh diameter of 0.25 mm and again mixed for 10 minutes. One part of the blend is pre-rubbed with 3.6 magnesiumstearate and the resulting abraded portion is added to the rest of the premixture over a screen having a mesh size of 0.25 mm. Then it is mixed again for 2 minutes in the double twist blender.

The blend thus obtained is pressed on a rotary tablet press having an 8 mm biconvex tool (radius of the curvature 9 mm) and a breaking kerf in the upper punch into tablet cores with a tensile strength of 100 N-150 N, an average mass of 244 mg and an abrasion of less than 0.5%.

300 g of the thus obtained tablet cores are sprayed in the fluidised bed by means of 2-substance nozzles with a suspension of 40 g Eudragit® L 12.5 (5.0 Eudragit® L dry substance), 0.05 g magnesiumstearate, 0.5 g talcum and 0.5 g triethylcitrate in 60 g 2-propanol.

304 g of the sprayed gel matrix tablets were obtained, corresponding to a total yield of 99%.

The content of propiverine-hydrochloride was determined by the method described in Example 6 to be 12.2%. This results in a content of 30.3 mg propiverine-hydrochloride per tablet. The content correction was taken into account when calculating the release. All other release parameters remained unchanged. The release values found are included in the Table of Example 5 as mean values of a 6-times determination.

Example 14

Comparative Bioavailability Study of Pellet Formulations of Examples 1, 2 and 3.1

In a clinical study the bioavailability and the pharmacokinetics of the pellet formulations of Examples 1, 2 and 3.1 were compared with each other.

For this purpose 6 test persons received the pellet formulations having 45 mg propiverine-hydrochloride each in a cross-over-design as a single dose. The blood levels were observed in 25 time periods in intervals of 20 min-12 hours for 48 hours in total. Propiverine and its main metabolite propiverine-N-oxide were determined with a validated HPLC method in the serum. For this 0.5 ml of the deep frozen serum or control samples, respectively, were combined after defrosting with 0.5 ml of phosphoric acid (4%) and then extracted by means of solid phases (Nexus cartridges, 1 ml, 30 mg). The eluates were evaporated to dryness and were taken up in 100:1 of mobile phase.

The chromatography was carried out on a commercially available equipment consisting of a pump, an autosampler, a column oven and a diode array detector at a flowrate of 1.2 ml/min, a column temperature of 40° C. and a detection wavelength of 202 nm, whereby the running time was about 5 minutes and the amount of sample or reference solution, respectively (empty serum sample treated under the same conditions with addition of propiverine-hydrochloride and propiverine-N-oxide) was 20 µl. As the stationary phase a reversed phase material was used (pre-column: LiChrocart 10×2 mm, LiChrospher 60, RP-select B, 5 µm (Merck); separating column: LiChrospher 60-5, select B, 125×2 mm (Macherey-Nagel)) and as the mobile phase a mixture of 70 parts per volume of acetonitrile and 30 parts per volume of phosphate buffer at pH 7.3 (2 mM potassium dihydrogenphosphate and disodiumhydrogenphosphate) was used. The registration and evaluation of the data was made by means of a Chromeleon Chromatography Data System. Under these analytic conditions the finding for propiverine was 99% and for propiverine-N-oxide 95%. At repeated measurements (n=5) of spiked serum samples (10 ng/ml propiverine or 20 ng/ml N-oxide, respectively) the variation coefficient of the measured concentrations was uniformly at 6%.

With the measured concentrations concentration-time-curves (blood levels) over a time period of 48 hours were drawn up and the area beneath these curves was calculated (Area Under the Curve=AUC). This parameter is a measure for the available amount of propiverine or propiverine-N-oxide, respectively, available in the blood circulation over time (bioavailability).

The AUC-values obtained with this bioavailability study for propiverine (see Table) show that a retardation of the drug release (Examples 2 and 3.1) does not result in a reduction of the bioavailability when compared with the immediately releasing pellet formulation (Example 1). Thus it is shown that by administration of propiverine in the form of the inventive retard formulations the availability of propiverine even from lower intestinal tracts is maintained. This means that with the release of propiverine in the lower intestinal tract the reduction of bioavailability which is typically known for basic drugs and which could be expected due to the known physicochemical properties of propiverine does not occur.

Contrary to the assumption that an unchanged propiverine resorption in the lower intestinal tracts may be the cause for this, surprisingly a reduced transformation to the propiverine-N-oxide (metabolite) was found as the reason. The amount (AUC) of the formed propiverine-N-oxide or of the ratio of metabolite/mother substance, respectively, decreases with increasing retardation (see Table). Thus, with the administration of retarded oral dosage forms of propiverine or the pharmaceutically acceptable salts thereof there is a reduced systemic strain on the organism through the undesired metabolisation product propiverine-N-oxide at equal bioavailability of the active agent propiverine.

It is clinically advantageous for an individual save dosage that the surprisingly discovered fact that the inter-individual variability of the amount of propiverine available (AUC), expressed as the variation coefficient (VK), very significantly decreases with the retardation (see Table). From 62% for the immediately releasing pellet formulation of Example 1 a reduction to 27% for the formulation of Example 3.1, which is the most retarded formulation, occurs.

Figure 2:
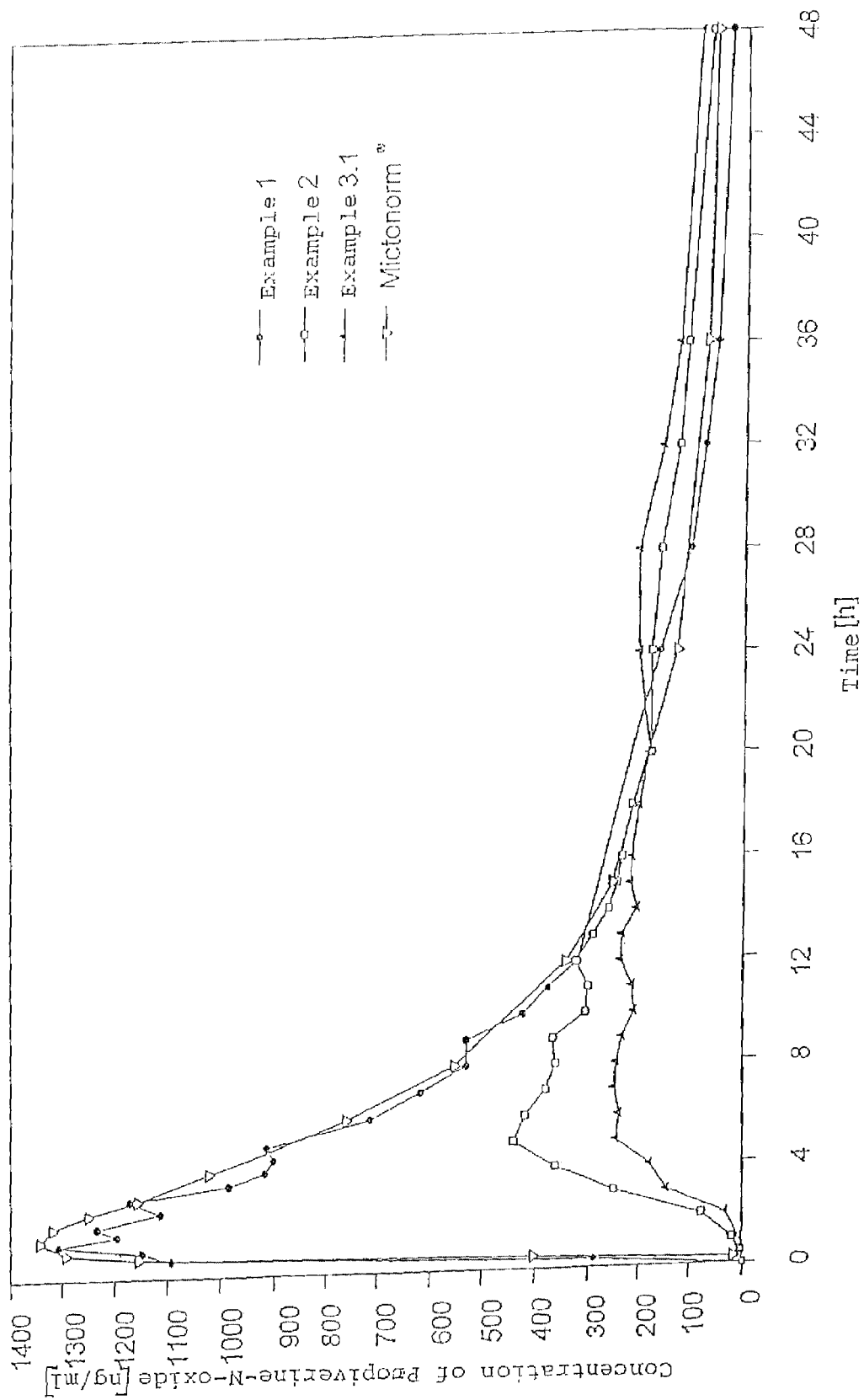
FIG. 2 plots the mean blood level value of propiverine-N-oxide over time after administration of several invention formulations versus a comparative commercial product, as described in Example 14.

In FIGS. 1 and 2 the concentration-time-courses (blood level) of propiverine or propiverine-N-oxide, respectively, after administration of the pellet formulations of Examples 1, 2 and 3.1 are illustrated as curves of the mean values of the 6 test persons. For comparative purposes the blood level after administration of 3 pills (15 mg propiverine-hydrochloride each) of the commercial product Mictonorm® (curves of the mean values of 34 test persons) are also illustrated. It can be seen that the pellet formulation of Example 1 may be taken as a reference for the commercial product.

The blood levels in FIGS. 1 and 2 show that the retardation results in a drastic reduction of the rate of the concentration increase of propiverine and propiverine-N-oxide. Additionally the height of the concentration maximum is reduced (Example 1 versus Example 2). With strong retardation, like in Example 3.1, a discrete concentration maximum can advantageously no longer be observed, i.e. a flattened blood level having relatively constant concentrations for a long period of time develops without decreasing the bioavailability by the retardation.

Furthermore it is noted that with the inventive dosage forms, for example that of Example 3.1, and under observation of the in vitro/in vivo correlation clinically effective blood levels can be realised for 24 hours.

Additionally one may expect a decrease in the frequency and/or severity of anticholinergic side effects caused by the avoidance of concentration peaks.

The results of the bioavailability study of the administration of the pellet formulations of Examples 1, 2 and 3.1 are illustrated in the following Table as the mean values.

TABLE

| | Bioavailability (AUC) of propiverine and propiverine-N-oxide | | |
| Parameter | Pellet formulation Example 1 | Pellet formulation Example 2 | Pellet formulation Example 3.1 |
| --- | --- | --- | --- |
| Propiverine AUC$_{0-48\,h}$[ng·h·ml$^{-1}$] | 1667 | 1705 | 1596 |
| VK[%] | 62 | 47 | 27 |
| Propiverine-N-oxide AUG$_{0-48\,h}$[ng·h·ml$^{-1}$] | 13076 | 8779 | 7829 |

TABLE-continued

Bioavailability (AUC) of propiverine and propiverine-N-oxide

| Parameter | Pellet formulation Example 1 | Pellet formulation Example 2 | Pellet formulation Example 3.1 |
|---|---|---|---|
| AUC-ratio Propiverine-N-oxide/Propiverine | 7.8:1 | 5.15:1 | 4.9:1 |
| AUG of propiverine-N-oxide referring to Example 1[%] | 100 | 71 | 63 |

Example 15

Bioequivalence Study of the Pellet Formulation of Example 3.2 Compared to the Commercial product Mictonorm®

In a bioequivalence study relevant for the admission and guideline-conformity the bioavailability of propiverine from the rapidly releasing commercial form (Mictonorm®) was compared with the pellet formulation of Example 3.2.

In doing so 12 male and 12 female healthy test persons received in a randomised manner in a cross-over-design over 7 days either 3 times daily one pill of Mictonorm® (15 mg propiverine-hydrochloride each) or 1 daily the pellet formulation of Example 3.2 (45 mg propiverine-hydrochloride). The change in medication took place after a washing-out phase of 15 days. At any seventh day the steady-state blood levels were observed in 28 time periods in intervals of 30 minutes-2 hours for 24 hours in total. Propiverine and its metabolite propiverine-N-oxide were determined in the serum by using the HPLC method as described in Example 13.

With the measured concentrations concentration time curves were drawn up under the conditions of a repeated dose (steady-state blood level) for a time period of 24 hours and the area beneath these curves was calculated (Area Under the Curve=$AUC_{0-24\ h,\ ss}$). This parameter is a measure for the amount of propiverine or propiverine-N-oxide, respectively, available in the blood circulation over 24 hours.

The results (see table data for bioequivalence) confirm the observation already made in Example 13 also for steady-state conditions, where the bioavailability of propiverine remains unchanged when it is administered in the form of retarded pellet formulations. There is bioequivalence between the commercial product (3×15 mg) and the pellet formulation of Example 3.2 (1×45 mg). Also the serum concentrations averaged over 24 hours at the same (see $C_{average}$ in the Table).

Furthermore the advantage to be expected from Example 13 of a reduced interindividual variability of the bioavailability of propiverine upon administration of the pellet formulation as compared to the commercial product is confirmed. The variation coefficient for the propiverine-AUC is only 15% for the pellet formulation (commercial product: 31%). Thus, an individualised dosage is clinically possible.

All 24 test persons show a decrease of the AUC of the propiverine-N-oxide upon administration of the pellet formulation compared to the commercial product in the intraindividual comparison. Thus, the result is a significantly smaller mean value of the AUC after administration of the pellet formulation compared to the commercial product. Also the averaged serum concentration over 24 hours is significantly lower upon administration of the pellet formulation (see $C_{average}$ in the Table). Thus the reduction of the strains with the clinically not necessary transformation product propiverine-N-oxide as described in Example 13 is confirmed for the conditions of the repeated administration (steady state).

The unchanged propiverine values for AUC and $C_{average}$ upon administration of the pellet formulation also prove that there is no accumulation of propiverine in the meaning of a blood level increase with time caused by the retarded release.

TABLE

Data of bioequivalence

| Parameter | Mictonorm ® 3 × 15 mg | Pellet formulation Example 3.2 1 × 45 mg |
|---|---|---|
| Propiverine $AUG_{0-24\ h}[ng \cdot h \cdot ml^{-1}]$ | 1677 | 1711 |
| VK[%] | 31 | 15 |
| Propiverine-N-oxide $AUC_{0-24\ h}[ng \cdot h \cdot ml^{-1}]$ | 11080 | 9316* |
| AUC-ratio Propiverine-N-oxide/Propiverine | 6.6:1 | 5.4:1 |
| AUC of propiverine-N-oxide referring to Mictonorm ® [%] | 100 | 84* |
| Propiverine $C_{average}[ng/ml]$ | 69.8 | 71.3 |
| Propiverine-N-oxide $C_{average}[ng/ml]$ | 462 | 388* |

*value is significantly less as compared to the administration of the commercial product Mictonorm Apart from the data for bioavailability and pharmacokinetics the side effects were also recorded in this study. In the following Table the frequency of the side effects is listed, for which a connection with the administration of propiverine has been classified by a physician as "safe", "probably" or at least as "possible". Upon the pellet formulation the frequency of the anticholinergic side effects typical for propiverine is reduced by nearly half (accommodation disorder and increased sensitivity to light) or by a quarter (dryness in the mouth), respectively. The total frequency of all side effects reported is reduced by about one third.

TABLE

Side effects

| Type of side effect (SE) | Mictonorm ® 3 × 15 mg | Pellet formulation Example 3.2 1 × 45 mg |
|---|---|---|
| Anticholinergic SE typical for propiverine: | | |
| a) Accommodation disorder/ increased sensitivity to light | 19 | 10 (53 %) |
| b) Dryness in the mouth | 20 | 15 (75 %) |
| Sum of other SE | 12 | 2 (66%) |
| Sum of all SE | 51 | 33 (65%) |

Example 16

In Vitro/In Vivo Correlation

For a simulation of the release process of active agents from various dosage forms the in vitro behaviour of the dosage forms is correlated with the in vivo data. If a correlation of the in vivo and in vitro data can be shown, a prediction of the in vivo release behaviour of other dosage forms is possible due to their in vitro release behaviour.

As a first prerequisite for an in vivo/in vitro correlation one has to demonstrate that the in vitro release mechanism is identical for the dosage forms observed. This is shown by the homomorphy (homogeneity of forms) of the corresponding profiles.

For this purpose the in vitro release data determined in accordance with Example 5 for the propiverine-hydrochloride containing pellet formulations described in Example 2 and Example 3.1 are illustrated by means of a Weibull function:

$$M_{(t)} = M_0 (1 - e^{\{(\lambda \cdot (t-\tau)) \beta\}})$$

$M_{(t)}$=Amount of propiverine-hydrochloride released at time t
wherein $M_0$=Total amount released of propiverine-hydrochloride [%]
$\lambda$=Release constant [1/h]
$\beta$=Increase factor (s(ope)
$\tau$=Shifting factor of the function on the time axis (lag-time) [h]

The adaptation of the curves was separately carried out for all dosage forms by means of a suitable software, for example HOEGIP-PC-Software, using the method of least error squares.

For the mathematical comparison of both in vitro release profiles the curves were standardised to 100% propiverine-hydrochloride released at termination of the experiments. Subsequently the time values were adapted by means of the following linear transformation:

$$t_{i,Ex2,trans} = (t_{i,Ex2} - \tau_{Ex.2}) \cdot (\lambda_{Ex2}/\lambda_{Ex3.1}) + \tau_{Ex3.1}$$

or $$t_{i,Ex3,trans} = (t_{i,Ex3.1} - \tau_{Ex3.1}) \cdot (\lambda_{Ex3.1}/\lambda_{Ex2}) + \tau_{Ex2}$$

wherein $t_{i,Ex.2,trans}$=Transformed time value of the i-th measured value at time $t_i$ of the dosage form according to Example 2

Figure 5:
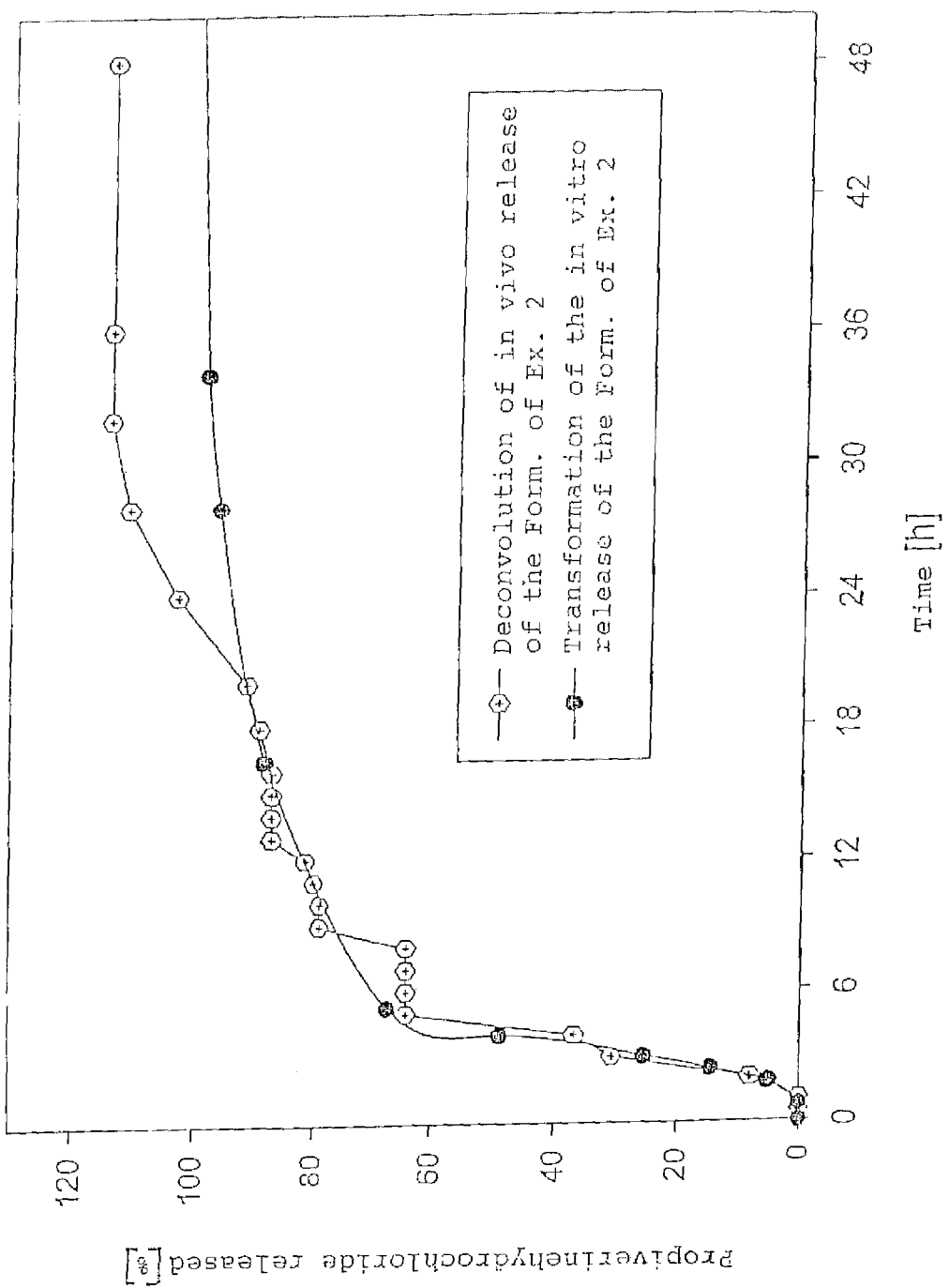
FIG. 5 comparatively plots in vivo and in vitro release profiles of the dosage form corresponding to Example 2 as described in Example 16.
Figure 6:
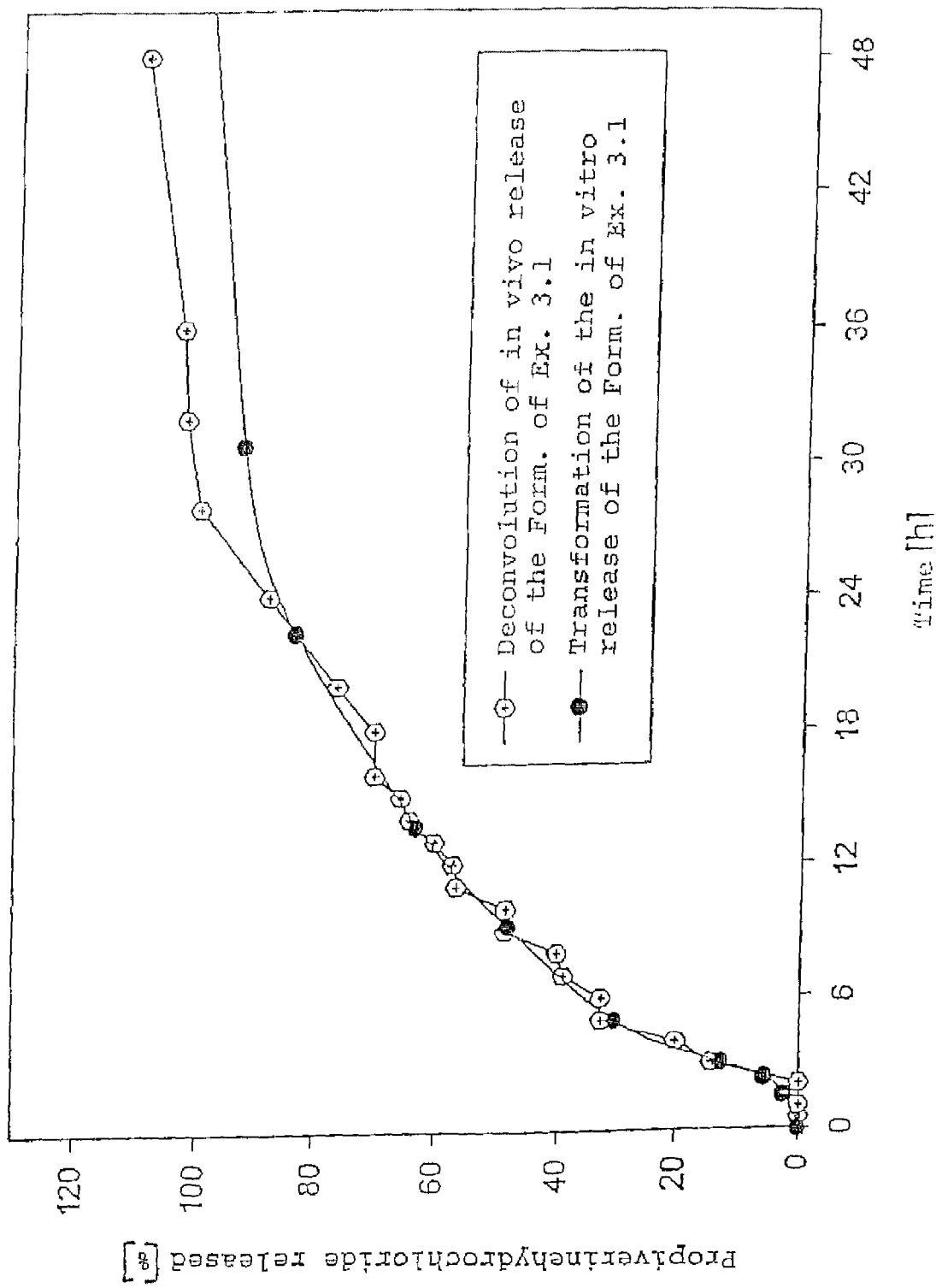
FIG. 6 comparatively plots in vivo and in vitro release profiles of the dosage form corresponding to Example 3.1, as described in Example 16.

For the in vivo or in vitro release profiles, respectively, of the dosage forms corresponding to Examples 2 and 3.1 the results of this procedure are illustrated in FIGS. 5 and 6. It can be recognised that the curves illustrated show a good conformity of the release profiles for both dosage forms observed. Thus, it could be demonstrated that the in vivo release profiles of Examples 2 and 3.1 can be determined by means of suitable in vitro release experiments. Therewith one may draw conclusions from the in vitro release profiles obtained to the in vivo release ratio of dosage forms not tested with humans and their usefulness for the production of clinically relevant blood levels and thus their relevance in practice can be predicted.

The invention claimed is:

1. A pharmaceutical composition for oral administration having prolonged release of an active agent, said active agent consisting of propiverine and/or one or more pharmaceutically acceptable salts thereof, the composition being adapted for once-a-day administration and having the following in vitro release, measured in 750 ml of 0.1 N hydrochloric acid during the first hour and subsequently measured in 750 ml USP buffer at pH=5.8 using a Ph. Eur. Basket method at 100 rpm and 37° C.:

| | | |
|---|---|---|
| 0-20% | proviverine, released after | 1 hour, |
| 10-45% | proviverine, released after | 3 hours, |
| 30-75% | proviverine, released after | 5 hours, |
| 40-85% | proviverine, relased after | 7 hours, |
| 50-95% | provivierine, relased after | 9 hours, |
| >60% | proviverine, relased after | 12 hours. |

2. The composition according to claim 1, wherein an amount of 4 mg to 60 mg of propiverine or the corresponding equivalent amount of a propiverine salt or a mixture thereof is included.

3. The composition according to claim 1 including at least one retarding agent.

4. The composition according to claim 3 additionally including at least one or more acidic substances having a pKa value of less than 6.65.

5. The composition according to claim 4, wherein the one or more acidic substances are present in an amount providing a ratio of 2:1 to 20:1 between the total amount of acidic substance and the propiverine or propiverine salt or mixtures thereof is, said ratio determined as monovalent acid equivalents to moles of propiverine.

6. The composition according to claim 4 wherein the acidic substance comprises an edible organic acid, a pharmaceutically acceptable salt of a multivalent acid, or a mixture of two or more of said acids and/or salts.

7. The composition according to claim 1 in the form of a multiple-unit formulation containing particles, said particles comprising an, optionally retarded, acid-containing core,
    the core being coated with propiverine, propiverine salt or mixture thereof, optionally with further acid components and adjuvants and
    the coated core being surrounded with a retardation layer made of generally gastric fluid and intestinal fluid insoluble polymers or of a combination of gastric fluid and intestinal fluid insoluble polymers with gastric fluid insoluble but intestinal fluid soluble polymers respectively,
    and wherein the composition is finally filled into capsules or sachets or is used as a component of a suspension for drinking.

8. The composition according to claim 1 in the form of a multiple-unit formulation, comprising spheroidal tablet formulations,
    the spheroidal tablet formulations comprising granular particles coated with gastric fluid insoluble but intestinal fluid insoluble and/or intestinal fluid soluble material and being pressed into tablets,
    wherein the granular particles are a compacted blend of one or more of propiverine, propiverine salts, one or more acidic substances, one or more spheronising agents, one or more lubricating agents and one or more tabletting adjuvants,
    and wherein the tablets may be additionally coated with retarding materials.

9. The composition according to claim 1 in the form of a single-unit formulation, comprising matrix tablet formulations,
    the matrix tablet formulations comprising a blend of propiverine, propiverine salt or mixture thereof, optionally one or several acidic substances, and matrix-forming retarding adjuvants, the matrix tablet formulations being pressed into tablets, and wherein the formulation is optionally provided with a coating made of polymers of acrylic and/or methacrylic acid derivatives or cellulose ethers, cellulose esters, vinylacetates, vinylpyrrolidones or shellac.

10. A method of treating a hypertonic functional state of the bladder comprising administering a composition as in claim 1.

11. A pharmaceutical composition for oral administration having prolonged release of an active agent, the active agent comprising propiverine and/or one or several pharmaceutically acceptable salts thereof in an amount of 4 mg to 60 mg of propiverine or the corresponding equivalent amount of a propiverine salt or a mixture thereof, being coated with one or more controlled releasing layers, said layer or layers comprising a retarding material insoluble in gastric fluid and insoluble in intestinal fluid, and/or a retarding material insoluble in gastric fluid and soluble in intestinal fluid, and/or being embedded in a controlled release matrix, which includes a swellable or insoluble material, the composition being administration and having the following in vitro release, measured in 750 ml of 0.1 N hydrochloric acid during the first hour and subsequently measured in 750 ml USP phosphate buffer at pH=5.8 using a Ph. Eur. Basket method at 100 rpm and 37° C.:

| 0-20% | proviverine, relased after | 1 hour, |
|---|---|---|
| 10-45% | proviverine, relased after | 3 hours, |
| 30-60% | proviverine, relased after | 5 hours, |
| 40-75% | proviverine, relased after | 7 hours, |
| 45-80% | provivierine, relased after | 9 hours, |
| 60-90% | proviverine, relased after | 12 hours. |

12. The composition according to claim 11, wherein the retarding material and/or the matrix material is selected from polymers and copolymers of acrylic and/or methacrylic acid esters, polymers and copolymers of vinylpyrrolidones, polymers and copolymers of vinylacetate, cellulose ethers, cellulose esters, polysaccharides, alginates, xanthanes, polyvinyl alcohols, cellulose acetate phthalates, monoglycerides, diglycerides, triglycerides, waxes, proteins or shellac.

13. The composition according to claim 11 additionally including at least one or more acidic substances having a pKa value of less than 6.65.

14. The composition according to claim 13, wherein the molar equivalent ratio between the total amount of acidic substance and propiverine or propiverine salt or mixtures thereof is 2:1 to 20:1.

15. The composition according to claim 13, including as the acidic substance an organic acid, selected from the group consisting of citric acid, tartaric acid, malic acid, maleic acid, succinic acid, ascorbic acid, fumaric acid, adipic acid, or pharmaceutically acceptable salts of said acids, or a mixture of any of said acids and/or salts.

16. The composition according to claim 15 where the acidic substance is citric acid.

17. The composition according to claim 11, in the form of a multiple unit formulation containing pellets, granules or compacted particles, wherein these particles comprise an acid containing core which is coated with propiverine or propiverine salt and/or with further acid components and adjuvants and this active agent containing core is surrounded with a retardation layer made of generally gastric fluid and intestinal fluid insoluble polymers or of a combination of gastric fluid and intestinal fluid insoluble polymers with gastric fluid insoluble but intestinal fluid soluble polymers respectively, and wherein the composition is finally filled into capsules or sachets or compacted with tableting adjuvants into tablets or is used as a component of a suspension for drinking.

18. The composition according to claim 11, in the form of a multiple unit formulation, comprising spheroidal tablet formulations spheroidal tablet formulations, the spheroidal tablet formulations comprising granular particles coated with gastric fluid insoluble but intestinal fluid insoluble and/or intestinal fluid soluble material and being pressed into tablets, wherein the granular particles are a compacted blend of one or more of propiverine, propiverine salts, one or more acidic substances, one or more spheronising agents, one or more lubricating agents and one or more tabletting adjuvants, and wherein the tablets may be additionally coated with retarding materials.

19. The composition according to claim 11, in the form of a single-unit formulation, comprising matrix tablet formulations, the matrix tablet formulations comprising a blend of propiverine, propiverine salt or mixture thereof, optionally one or several acidic substances, and matrix-forming retarding adjuvants, the matrix tablet formulations being pressed into tablets, and wherein the formulation is optionally provided with a coating made of polymers of acrylic and/or methacrylic acid derivatives or cellulose ethers, cellulose esters, vinylacetates, vinylpyrrolidones or shellac.

* * * * *

UNITED STATES PATENT AND TRADEMARK OFFICE
CERTIFICATE OF CORRECTION

| | | |
|---|---|---|
| PATENT NO. | : 7,943,176 B2 | Page 1 of 4 |
| APPLICATION NO. | : 10/492270 | |
| DATED | : May 17, 2011 | |
| INVENTOR(S) | : Thomas Gramatte et al. | |

It is certified that error appears in the above-identified patent and that said Letters Patent is hereby corrected as shown below:

Column 1, line 63, please change "resort in prolongated" to -- resorb in protonated --

Column 2, line 35, please change "physiochemical" to -- physicochemical --

Column 2, line 66, please change "from" to -- form --

Column 3, line 11, please change "WO 0737202" to -- WO 9637202 --

Column 3, line 34, please change "of" to -- for --

Column 5, line 24, please change "matrix forming" to -- matrix-forming --

Column 5, line 59, please change "fluidized be" to -- fluidised bed --

Column 6, line 23, please change "microns" to -- micronised --

Column 8, line 14, please change "table" to -- tablet --

Column 9, line 5, please change "slats" to -- salts --

Column 10, line 51, please change "Kollidor" to -- Kollidon --

Column 10, line 64, please change "210" to -- 210 g --

Column 11, line 8, please change "35" to -- 35 g --

Column 11, line 11, please change "2585 g" to -- 2583 g --

Column 11, line 15, please change "12.5" to -- 12.5 g --

Signed and Sealed this
Thirteenth Day of March, 2012

David J. Kappos
*Director of the United States Patent and Trademark Office*

CERTIFICATE OF CORRECTION (continued)
U.S. Pat. No. 7,943,176 B2

Column 11, line 61, please change "65" to -- 65 g --

Column 13, line 36, please change "of thus" to -- of the thus --

Column 16, line 48, please change "were" to -- are --

Column 17, line 27, please change "electivity" to -- selectivity --

Column 18, line 12, please change "90 g" to -- 90 g dry substance --

Column 19, line 7, please change "990 g" to -- 90 g --

Column 19, line 20, please change "30000 g" to -- 3000 g --

Column 20, line 43, please change "The" to -- Then --

Column 20, line 61, please change "40° C." to -- 40°C --

Column 24, in the table, please change "AUG" to -- AUC --

Column 25, in the table, please change "AUG" to -- AUC --

Column 25, line 28, please change "15 days" to -- 14 days --

Column 26, line 28, please change "AUG" to -- AUC --

Column 27, line 21, please change "$M_{(t)}=M_0(1-e^{\{(\lambda \cdot (i-\tau))\beta\}})$" to -- $M_{(t)}=M_0(1-e^{\{(\lambda \cdot\ (i-\tau))\beta\}})$ --

Column 27, line 28, please change "scope" to -- slope --

At Column 27, after line 48, please insert the following text which was omitted from the issued patent but present at page 49 of the application as filed:

-- $t_{i,\ Ex.\ 2}$ = Not transformed time period of the i-th measured value of the in vivo release of Example 2

$\tau_{Ex2}$ = Lag-time of the release of Example 2

$\lambda_{P2}$ = Release contrasts of the measured values of the dosage form according to Example 2

The same is true for the indices of Example 3.1.

Figure 3:
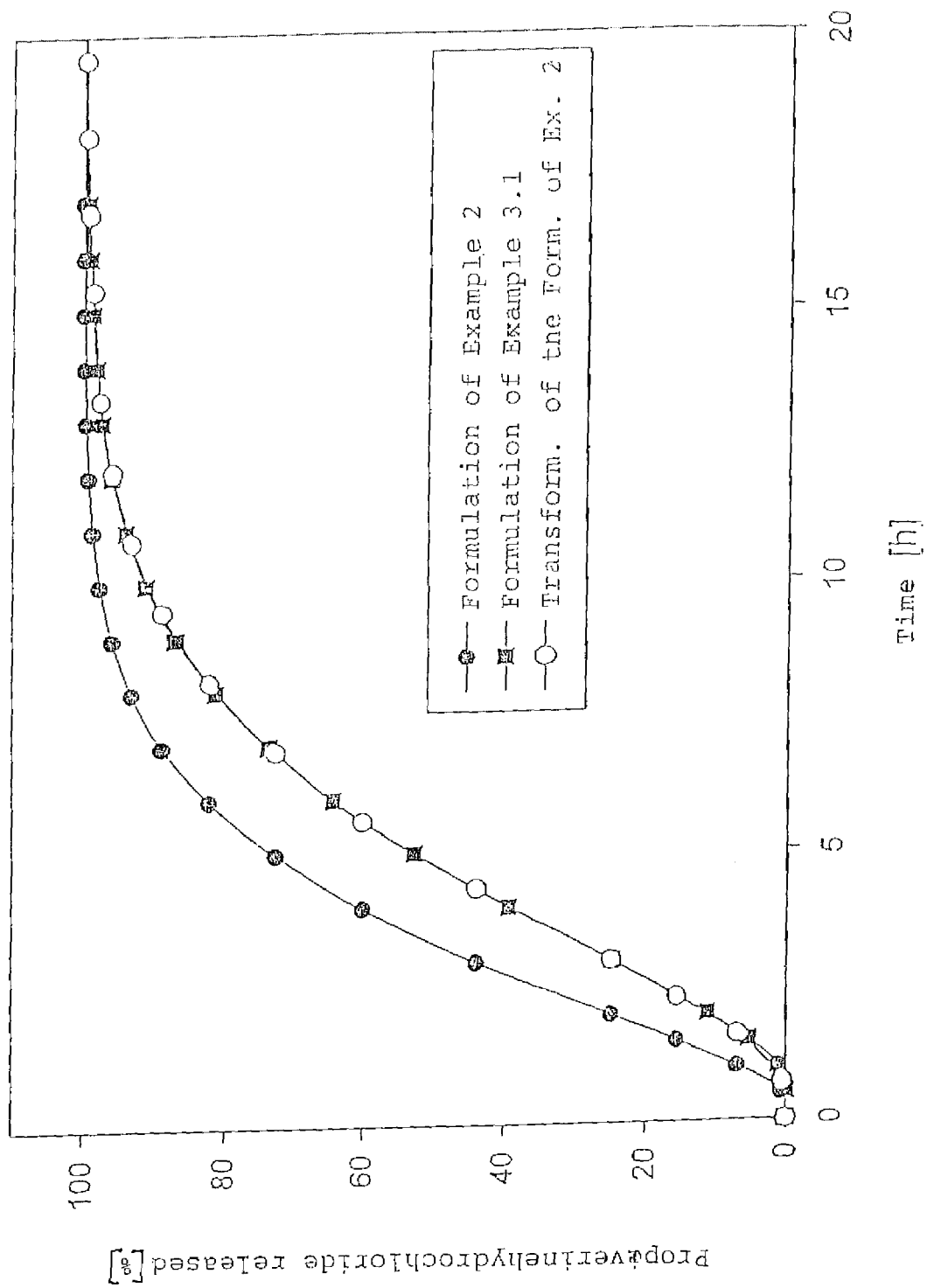
FIG. 3 plots the homomorphy transformation from Example 2 to Example 3.1 as described in Example 16.
Figure 4:
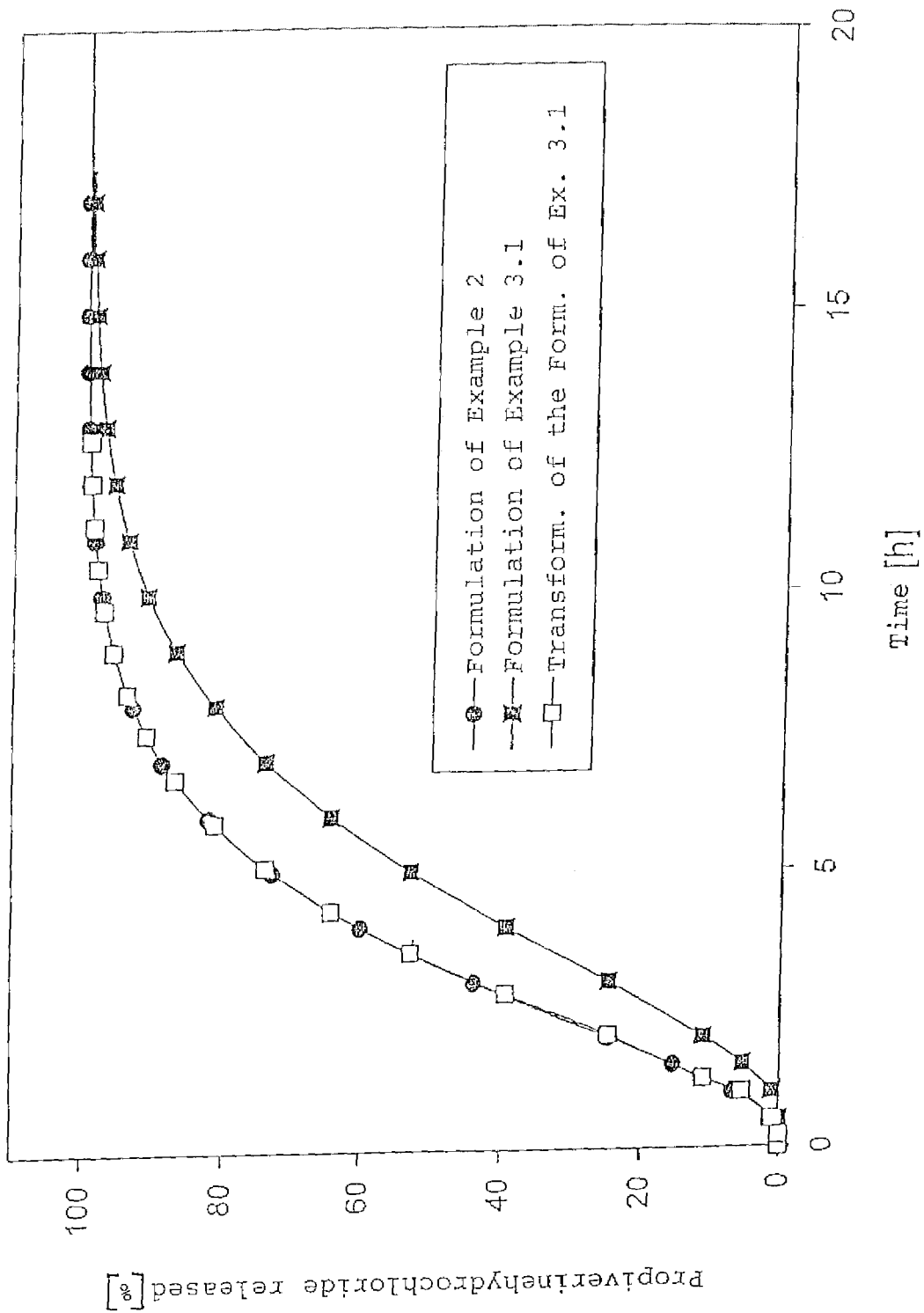
FIG. 4 plots the homomorphy transformation from Example 3.1 to Example 2 as described in Example 16.

The results are illustrated in Figures 3 (transformation from Example 2 to Example 3.1) and 4 (transformation from Example 3.1 to Example 2). The correlation coefficients for the transformation were 0.9997 for the figure from Example 2 to Example 3.1 or 0.99969, respectively, for the transformation from Example 3.1 to Example 2. This value demonstrates the nearly exact homogeneity of form of the in vitro release profiles
observed. The prerequisite for a comparison of the in vivo data with the in vitro data is thus given.

In a next step the average serum levels of propiverine from 6 test persons after one administration of the dosage forms corresponding to Example 2 or Example 3.1, respectively, as already illustrated in Example 13, were added by means of the method of deconvolution to the cumulative in vivo release profile. For this purpose the active agent amounts available per time unit each in the serum are observed over time considering the metabolic decomposition of the active agent.

Subsequently it was tried to depict the in vitro release profiles thus obtained by means of the linear transformation of the time axis already described above onto the in vivo release profiles. --

Column 28, lines 6-11, please change:

"
| | | |
|---|---|---|
| 0-20% | proviverine, released after | 1 hour, |
| 10-45% | proviverine, released after | 3 hours, |
| 30-75% | proviverine, released after | 5 hours, |
| 40-85% | proviverine, relased after | 7 hours, |
| 50-95% | provivierine, relased after | 9 hours, |
| >60% | proviverine, relased after | 12 hours. |
"

to

| | | |
|---|---|---|
| 0 - 20% | propiverine, released after | 1 hour, |
| 10 - 45% | propiverine, released after | 3 hours, |
| 30 - 60% | propiverine, released after | 5 hours, |
| 40 - 75% | propiverine, released after | 7 hours, |
| 50 - 80% | propiverine, released after | 9 hours, |
| 60 - 90% | propiverine, released after | 12 hours. |

--  --

Column 29, lines 31-36, please change:

"
| | | |
|---|---|---|
| 0-20% | proviverine, relased after | 1 hour, |
| 10-45% | proviverine, relased after | 3 hours, |
| 30-60% | proviverine, relased after | 5 hours, |
| 40-75% | proviverine, relased after | 7 hours, |
| 45-80% | provivierine, relased after | 9 hours, |
| 60-90% | proviverine, relased after | 12 hours. |
"

CERTIFICATE OF CORRECTION (continued)
U.S. Pat. No. 7,943,176 B2 to

0 - 20 % propiverine, released after 1 hour,

10 - 45 % propiverine, released after 3 hours,

30 - 60 % propiverine, released after 5 hours,

40 - 75 % propiverine, released after 7 hours,

50 - 80 % propiverine, released after 9 hours,

60 - 90 % propiverine, released after 12 hours.